(12) United States Patent
Nakanishi et al.

(10) Patent No.: US 8,168,764 B2
(45) Date of Patent: May 1, 2012

(54) POLYFUNCTIONAL COMPOUND, OPTICAL RECORDING MATERIAL, OPTICAL RECORDING MEDIUM, OPTICAL RECORDING/REPRODUCING APPARATUS, OPTICAL WAVEGUIDE MATERIAL, AND PHOTO-ALIGNMENT FILM MATERIAL

(75) Inventors: Sadahiro Nakanishi, Osaka (JP); Mitsuru Ueda, Tokyo (JP)

(73) Assignee: Nitto Denko Corporation, Ibaraki-shi, Osaka (JP)

( * ) Notice: Subject to any disclaimer, the term of this patent is extended or adjusted under 35 U.S.C. 154(b) by 396 days.

(21) Appl. No.: 12/307,079

(22) PCT Filed: Jul. 3, 2007

(86) PCT No.: PCT/JP2007/063308
§ 371 (c)(1),
(2), (4) Date: Dec. 30, 2008

(87) PCT Pub. No.: WO2008/007582
PCT Pub. Date: Jan. 17, 2008

(65) Prior Publication Data
US 2009/0209741 A1    Aug. 20, 2009

(30) Foreign Application Priority Data

Jul. 11, 2006   (JP) .................................. 2006-190185

(51) Int. Cl.
*C07C 245/08* (2006.01)
*G02B 5/30* (2006.01)
*G02B 1/10* (2006.01)

(52) U.S. Cl. ........ 534/575; 534/806; 534/810; 534/852; 427/163.1; 359/491.01; 359/492.01

(58) Field of Classification Search ........................ None
See application file for complete search history.

(56) References Cited

U.S. PATENT DOCUMENTS

| 6,423,799 | B1 | 7/2002 | Berneth et al. |
| 6,909,684 | B2 | 6/2005 | Kawano et al. |
| 7,884,167 | B2 | 2/2011 | Nakanishi et al. |
| 2002/0163873 | A1 | 11/2002 | Kawano et al. |
| 2007/0242322 | A1* | 10/2007 | Fukuda et al. .................... 359/3 |
| 2009/0182107 | A1 | 7/2009 | Nakanishi et al. |
| 2011/0046358 | A1 | 2/2011 | Nakanishi et al. |
| 2011/0098454 | A1 | 4/2011 | Nakanishi et al. |

FOREIGN PATENT DOCUMENTS

| CA | 2366846 A1 | 2/2000 |
| JP | 2000-514468 A | 10/2000 |
| JP | 2002-265541 A | 9/2002 |
| JP | 2002-539476 A | 11/2002 |
| JP | 2002-351288 A | 12/2002 |
| JP | 2005-089371 A | 4/2005 |
| JP | 2006-219383 A | 8/2006 |
| JP | 2008-019178 A | 1/2008 |
| WO | 97/44365 A1 | 11/1997 |
| WO | 00/54112 A1 | 9/2000 |

OTHER PUBLICATIONS

Machine Translation of JP 2006-219383, Aug. 24, 2006.*
Kaemmerer et al., Chemical Abstracts, 69:67773, 1968.*
Angiolini, L. et al., Polymer, 6, 1875-1885, available online Feb. 7, 2006.*
Ringdorf, Helmut et al; "Electro-optical effects of azo dye containing liquid crystalline copolymers"; Makromol. Chem. 185, pp. 1327-1334, 1984.
Coufal, et al. (Eds.); "Holographic Data Storage"; Springer (publisher), Photoaddressable Polymers, p. 209-228, 2000.
O. Tsutsumi et al., "Photochemical Phase-Transition Behavior of Polymer Liquid Crystals Induced by Photochemical Reaction of Azobenzenes with Strong Donor-Acceptor Pairs", Journal of Physical Chemistry B, 1998, pp. 2869-2874, vol. 102, Cited in ISR.
Y. Wu et al., "Photoinduced Chirality in Thin Films of Achiral Polymer Liquid Crystals Containing Azobenzene Chromophores", Macromolecules, 2004, pp. 6801-6805, vol. 37, Cited in ISR.
International Search Report of PCT/JP2007/063308, Mailing Date of Aug. 7, 2007.
Japanese Office Action dated Nov. 16, 2011, issued in corresponding Japanese Patent Application No. 2006-190185.

* cited by examiner

*Primary Examiner* — Fiona T Powers
(74) *Attorney, Agent, or Firm* — Westerman, Hattori, Daniels & Adrian, LLP

(57) ABSTRACT

Provided is a polyfunctional compound which can be used as an optical recording material in which a large quantity of information data can be recorded optically at a high density, which can be used as an optical waveguide material using a refractive index difference occurring between a light-irradiated part and a part not irradiated with light, and which is capable of forming a film and can be used as a photo-alignment film material having excellent photosensitivity.

24 Claims, 5 Drawing Sheets

POLYFUNCTIONAL COMPOUND, OPTICAL RECORDING MATERIAL, OPTICAL RECORDING MEDIUM, OPTICAL RECORDING/REPRODUCING APPARATUS, OPTICAL WAVEGUIDE MATERIAL, AND PHOTO-ALIGNMENT FILM MATERIAL

TECHNICAL FIELD

The present invention relates to a polyfunctional compound and a use thereof. More specifically, the present invention relates to a polyfunctional compound having a photoisomerization group which causes structural isomerization by light irradiation.

The structural isomerization by light irradiation is a reversible reaction, and if a light-irradiated part is heated or the like, the part can be returned to an original state. Therefore, the polyfunctional compound is also applicable to a dynamic optical functional material such as an optical switch. Specifically, the polyfunctional compound can be used as an optical recording material in which a large quantity of data information can be recorded optically at high density. Thus, the present invention also relates to an optical recording medium and an optical recording/reproducing apparatus using the polyfunctional compound as an optical recording material.

Further, when the polyfunctional compound is irradiated with light, a refractive index may be modulated due to the photoisomerization of a photoisomerization site, and a refractive index difference can be caused between the light-irradiated part and a part not irradiated with light. Therefore, the polyfunctional compound can be applied to an optical waveguide. Thus, the present invention also relates to an optical waveguide material using the polyfunctional compound.

Further, the polyfunctional compound can form a film, and can be changed to any appropriate shape by spin coating, thermal melting, or the like. Therefore, the polyfunctional compound is capable of forming a film and is excellent in photosensitivity. Thus, the present invention also relates to a photo-alignment film material using the polyfunctional compound.

BACKGROUND ART

Recently, hologram recording has been studied actively since the hologram recording enables high-density recording, multi-recording, and the like. As the hologram recording, recording using an amplitude hologram utilizing a change in transmittance of a recording material, recording using a phase hologram utilizing a change in a refractive index and a change in unevenness of a recording material are known.

Among the recording materials used in hologram recording, a hologram recording material whose refractive index changes due to light irradiation (hereinafter may be referred to as "photorefractive material") has been studied extensively. In particular, an organic photorefractive material has been studied actively because of the ease of forming into any appropriate shape and the ease of regulating a response wavelength.

In the photorefractive material, charge is generated by light irradiation, the generated charge moves to be trapped, an internal electric field is generated consequently, and a refractive index changes due to the Pockels effect caused by the internal electric field. A hologram is formed by the change in refractive index.

However, in the organic photorefractive material, it is required that molecules be aligned so as to express the Pockels effect effectively, which requires an external electric field. The necessity for an external electric field is an important problem in the application of the organic photorefractive material.

As a hologram recording material which does not require an external electric field, an organic material having an azobenzene skeleton is known. In hologram recording, the photoisomerization reaction of an azobenzene skeleton plays an important role. When a film using such a material is irradiated with linearly polarized light, the azobenzene skeleton is realigned due to the isomerization cycle of trans-cis-trans.

The azobenzene skeleton absorbs light corresponding to a p-p* transition, and is excited from a thermally stable trans form to a cis form to cause the modulation of a refractive index. The cis form generated by photoexcitation returns to a trans form spontaneously due to thermal relaxation. Therefore, when natural light is used as a light source, a large modulation of a refractive index cannot be expected. However, the following is known. When polarized light is used as a light source, only a trans form a zobenzene skeleton having an electric field matched with an electric vector of polarized light is excited, and further, when the excited cis form azobenzene skeleton returns to a trans form due to thermal relaxation, the excited cis form azobenzene skeleton returns to a trans form having an electric field perpendicular to the electric vector of polarized light. Thus, the azobenzene skeleton that cannot be excited is accumulated in the light-irradiated part to cause birefringence, and the modulation of a refractive index due to the birefringence is caused (Weigert effect: for example, see Next-generation polymer/supermolecule controlling light, NTS (2000) edited by The Society of Polymer Science, Japan) Further, when a light-irradiated site is heated or the like, the light-irradiated site changes to a trans form having random alignment (electric field) in an initial state to eliminate birefringence due to the molecular movement, whereby data can be written again. Due to the change in alignment, photoisomerization, i.e., birefringence and dichroism are induced, whereby hologram recording can be performed. Thus, an organic material having an azobenzene skeleton has a potential for a rewritable optical recording material, and in particular, for a hologram recording material.

The modulation of a refractive index of only an azo dye increases in proportion to the amount of the azo dye, so a material having large absorption is required for obtaining a large modulation of a refractive index, and a large output laser is required.

However, it has been reported that, when a liquid crystalline compound as well as an azo dye are used, large induction of birefringence is possible even with a relatively small absorption amount (for example, see Non-Patent Document 1). More specifically, for example, when a mixture of an azo dye and a liquid crystalline compound is used, liquid crystalline molecules are further aligned from the azo dye aligned by polarization, whereby extremely large birefringence can be expressed, and there is an effect of enhancing the modulation of a refractive index.

As such a hologram recording material, hologram recording materials using a polymer containing azobenzene, which have an azobenzene site and a liquid crystal site with a particular structure at a side chain and have an acrylate or methacrylate main chain, have been disclosed (for example, see Patent Documents 1 and 2). However, the materials are insufficient for an optical recording medium in both sensitivity (recording speed) and recording density.

Further, Non-Patent Document 1 describes a polymer compound suitable for hologram recording. However, in order to realize writing in a short period of time, it is necessary to induce anisotropy previously over the entire medium, and pre-treatment therefor is required. Further, multi-recording results of hologram using a recording medium having a thickness of 500 μm are described, but it takes 30 seconds for hologram recording, which cannot be considered to be sufficient as a practical recording speed.

Thus, a polymer material containing an azobenzene skeleton that has been reported is difficult to be used as a volume hologram material forming a plurality of holograms in an optical recording medium. More specifically, it is difficult to produce a thick film medium that achieves high-speed recording of digital data by realizing a high-diffraction efficiency, and a thickness of about 40 μm is a limit as a practical medium (for example, see Non-Patent Document 2).

Further, in the case of using liquid crystallinity, light scattering caused by liquid crystallinity occurs, so that the liquid crystallinity is difficult to be applied to an application using a transparent material. For example, a material can also be made transparent by uniformly aligning liquid crystal by a uniform alignment technique. However, uniform alignment can be performed only with a thickness of about several μm, so the liquid crystallinity is not suitable in the case of using a thick film.

Further, according to a method of using a liquid crystalline polymer, a polymer compound solution exhibiting thermotropic liquid crystallinity is applied to a substrate subjected to alignment treatment, and thereafter, the substrate is heat-treated at a temperature at which the liquid crystalline polymer exhibits liquid crystallinity to obtain desired alignment. After the alignment, the liquid crystalline polymer is kept in a glass state, whereby the alignment is immobilized. However, when the liquid crystalline polymer is applied to the substrate subjected to alignment treatment, the liquid crystalline polymer is applied while being dissolved in a solvent. Therefore, the liquid crystalline polymer cannot be applied to a substrate having low solvent resistance such as some kinds of plastic. Further, the liquid crystalline polymer has less compatibility with another component, so a synthetic operation such as copolymerization needs to be performed, for example, in order to combine functional sites of a liquid-crystal group, an azobenzene skeleton, and the like.

As a method of obtaining a liquid crystal compound excellent in compatibility, the idea of vitrified liquid crystal has been reported. A liquid crystal compound expressing vitrified liquid crystal has a plurality of liquid-crystal groups at ends, and the liquid-crystal groups and a core portion are connected via connecting groups. Due to such a structure, the enhancement of solubility and uniform application performance to some degree are recognized.

The uniform application performance is exhibited effectively in the case where a liquid crystal phase expressed by a liquid crystal material is only a nematic liquid crystal phase. Conversely, when a liquid crystal phase contains a phase close to crystal such as a smectic phase, uniform application becomes difficult due to the crystallization and smectic liquid crystallization during the application to a substrate and alignment treatment. Therefore, in vitrified liquid crystal, a liquid crystal compound having a lateral substituent is designed so as to express a single nematic liquid crystal phase by decreasing the crystallinity of liquid crystal, whereby uniform application performance is ensured. However, in a liquid crystal compound having a liquid-crystal group with a simple structure having no lateral substituent, a single nematic liquid crystal phase is not expressed, and the development of such a liquid crystal compound is desired.
Patent Document 1: JP 2000-514468 A
Patent Document 2: JP 2002-539476 A Non-Patent Document 1: H. Ringsdorf and H-W. Schmidt, Makromol. Chem, 1327-1334 (1984)
Non-Patent Document 2: H. J. Coufal, D. Psaltis G. T. Sincerbox eds.: Holographic Data Storage, Springer, p. 222 (2000)

DISCLOSURE OF THE INVENTION

Problems to be Solved by the Invention

An object of the present invention is to provide a polyfunctional compound which can be used as an optical recording material in which a large quantity of data information can be recorded optically at a high density, which can be used as an optical waveguide material using a refractive index difference occurring between a light-irradiated part and a part not irradiated with light, and which is capable of forming a film and can be used as a photo-alignment film material having excellent photosensitivity.

Means for Solving the Problems

A polyfunctional compound of the present invention includes a chemical structure represented by Formula (1):

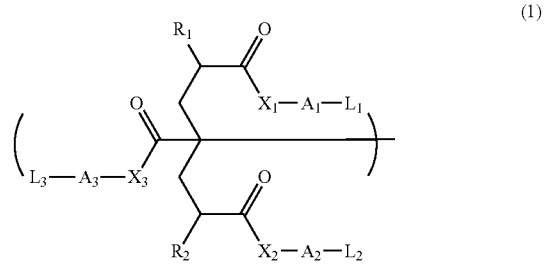

where: $R_1$ and $R_2$ each independently represent any of H, $CH_3$, and Cl; $X_1$ to $X_3$ each independently represent any of —O—, —NH—, and —N(alkyl group)-; $A_1$ to $A_3$ each independently represent a divalent connecting group; and $L_1$ to $L_3$ each independently represent any of a photoisomerization group, a liquid-crystal group, and H, and at least one of $L_1$ to $L_3$ represents a photoisomerization group.

In a preferred embodiment, the polyfunctional compound of the present invention is represented by Formula (1a):

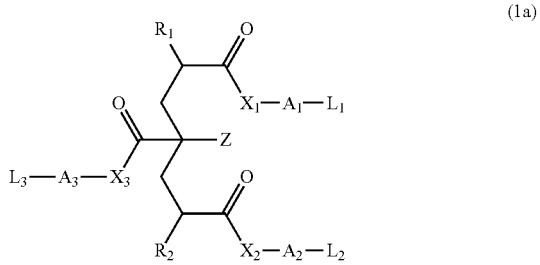

where: $R_1$ and $R_2$ each independently represent any of H, $CH_3$, and Cl; Z represents any of H, CN, and $COCH_3$; $X_1$ to $X_3$ each independently represent any of —O—, —NH—, and —N(alkyl group)-; $A_1$ to $A_3$ each independently represent a divalent connecting group; and $L_1$ to $L_3$ each independently represent any of a photoisomerization group, a liquid-crystal group, and H, and at least one of $L_1$ to $L_3$ represents a photoisomerization group.

In a preferred embodiment, the polyfunctional compound of the present invention is represented by Formula (1b):

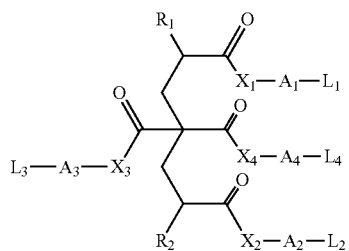

where: $R_1$ and $R_2$ each independently represent any of H, $CH_3$, and Cl; $X_1$ to $X_4$ each independently represent any of —O—, —NH—, and —N(alkyl group)-; $A_1$ to $A_4$ each independently represent a divalent connecting group; and $L_1$ to $L_4$ each independently represent any of a photoisomerization group, a liquid-crystal group, and H, and at least one of $L_1$ to $L_4$ represents a photoisomerization group.

In a preferred embodiment, the polyfunctional compound of the present invention is represented by Formula (1c):

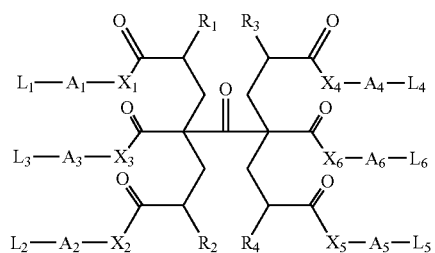

where: $R_1$ to $R_4$ each independently represent any of H, $CH_3$, and Cl; $X_1$ to $X_6$ each independently represent any of —O—, —NH—, and —N(alkyl group)-; $A_1$ to $A_6$ each independently represent a divalent connecting group; and $L_1$ to $L_6$ each independently represent any of a photoisomerization group, a liquid-crystal group, and H, and at least one of $L_1$ to $L_6$ represents a photoisomerization group.

In a preferred embodiment, the polyfunctional compound of the present invention includes the photoisomerization group having a structure represented by Formula (2):

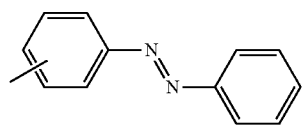

where: each aromatic ring may have one or more substituents.

In a preferred embodiment, the polyfunctional compound of the present invention includes the liquid-crystal group having a structure represented by any of Formulae (3a) to (3g):

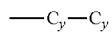 (3a)

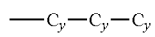 (3b)

—$C_y$—Y—$C_y$ (3c)

—$C_y$—Y—$C_y$—Y—$C_y$ (3d)

—$C_y$—C≡C—$C_y$ (3e)

—$C_y$—C≡C—$C_y$—C≡C—$C_y$ (3f)

—$C_y$—Y—$C_y$—C≡C—$C_y$ (3g)

where: Y's represent any of —COO—, —OCO—, —CONH—, CON(alkyl)-, and —CH=N—; and Cy's each independently represent a phenyl ring, a naphthyl ring, a biphenyl ring, and a cyclohexyl ring which may have at least one substituent selected from F, CN, an alkoxy group, and an alkyl group.

According to another aspect of the present invention, an optical recording material is provided. The optical recording material of the present invention includes the polyfunctional compound of the present invention.

According to another aspect of the present invention, an optical recording medium is provided. The optical recording medium of the present invention includes an optical recording layer containing the optical recording material of the present invention.

According to another aspect of the present invention, an optical recording/reproducing apparatus is provided. The optical recording/reproducing apparatus of the present invention includes the optical recording medium of the present invention.

According to another aspect of the present invention, an optical waveguide material is provided. The optical waveguide material of the present invention includes the polyfunctional compound of the present invention.

According to another aspect of the present invention, a photo-alignment film material is provided. The photo-alignment film material of the present invention includes the polyfunctional compound of the present invention.

EFFECTS OF THE INVENTION

According to the present invention, a polyfunctional compound can be provided, which can be used as an optical recording material in which a large quantity of data information can be recorded optically at a high density, which can be used as an optical waveguide material using a refractive index difference occurring between a light-irradiated part and a part not irradiated with light, and which is capable of forming a film and can be used as a photo-alignment film material having excellent photosensitivity. Further, an optical recording material, an optical recording medium, an optical recording/reproducing apparatus, an optical waveguide material, and a photo-alignment film material using such a polyfunctional compound can be provided.

DETAILED DESCRIPTION OF THE INVENTION

Figure 1:
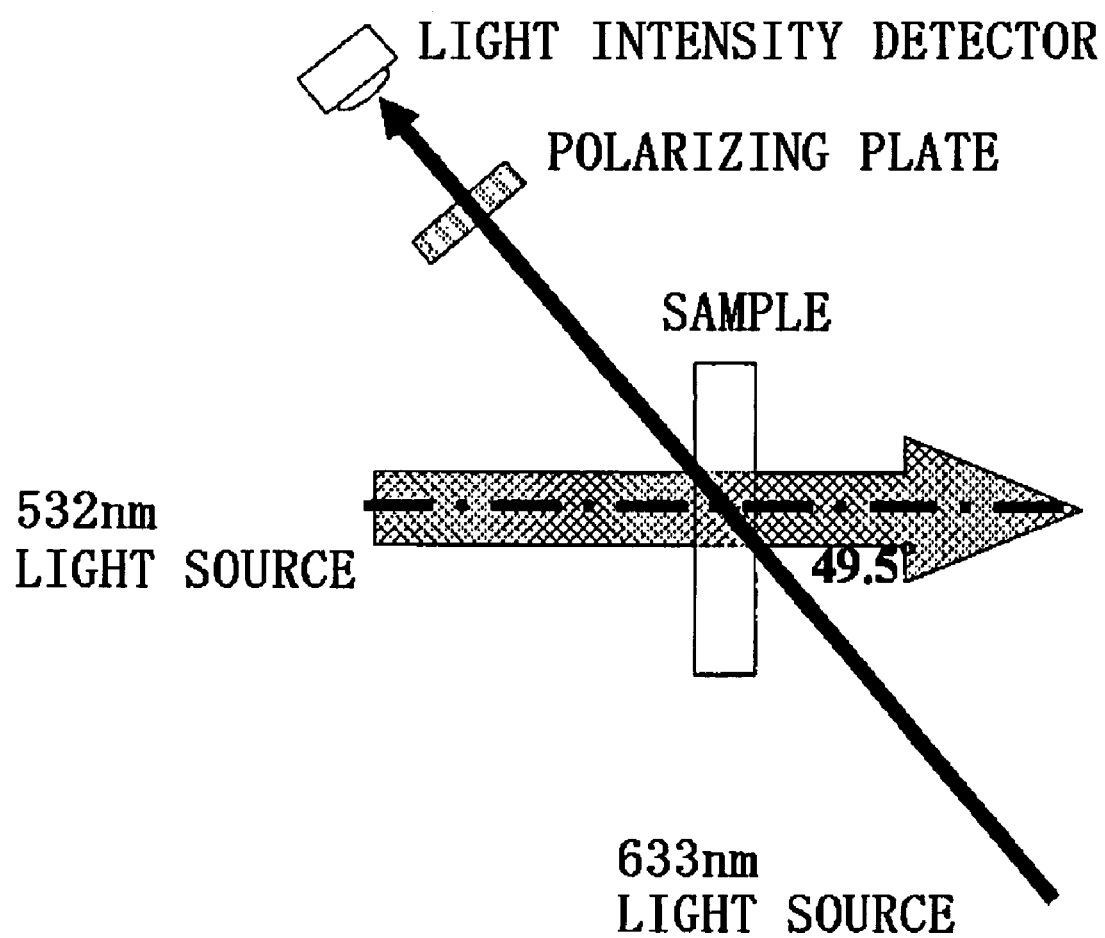
FIG. 1 is a schematic diagram of an optical experiment regarding the induction of birefringence by single flux exposure.

Hereinafter, the present invention is described by way of preferred embodiments, but the present invention is not limited to those embodiments. In the specification of the present invention, "(meth)acrylic acid" refers to acrylic acid or methacrylic acid.

<<Polyfunctional Compound>>

The polyfunctional compound of the present invention includes a chemical structure represented by Formula (1).

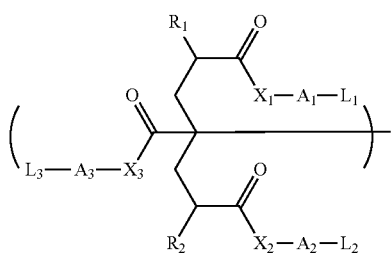

(1)

In Formula (1), $R_1$ and $R_2$ each independently represent any of H, $CH_3$, and Cl.

In Formula (1), $X_1$ to $X_3$ each independently represent any of —O—, —NH—, and —N(alkyl group)-.

In Formula (1), $A_1$ to $A_3$ each independently represent a divalent connecting group. The divalent connecting group in the present invention refers to an alkylene group or a single bond having 1 to 12 carbon atoms. One —$CH_2$— present in the alkylene group or two or more —$CH_2$— which are not adjacent to each other may be replaced by —O—. Further, the alkylene group may contain a benzoate skeleton or an amide benzoate skeleton such as —O-Ph-CO—, —NH-Ph-CO—, or —N(alkyl group) Ph-CO—. Herein, Ph represents a benzene ring which may be substituted.

In Formula (1), $L_1$ to $L_3$ each independently represent any of a photoisomerization group, a liquid-crystal group, and H, and at least one of $L_1$ to $L_3$ represents a photoisomerization group.

As the photoisomerization group, any suitable photoisomerization group can be selected as long as a photoisomerization site causes an isomerization reaction by light irradiation. Examples of the photoisomerization group include a group having an azobenzene skeleton and a group having a stilbene skeleton, causing trans-cis isomerization. The group having an azobenzene skeleton is preferred in the present invention. Specifically, a photoisomerization group having a structure represented by Formula (2) is preferred.

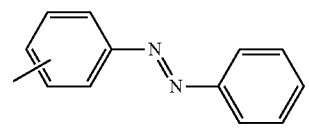

(2)

In Formula (2), each aromatic ring may have one or more substituents. Further, at last two substituents of each aromatic ring may be connected to form a new ring structure.

As the liquid-crystal group, any suitable liquid-crystal group can be selected. In the present invention, a liquid-crystal group having a structure represented by any of Formulae (3a) to (3g) is preferred.

(3a)

(3b)

(3c)

(3d)

(3e)

(3f)

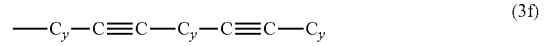

(3g)

In Formulae (3a) to (3g): Y's represent any of —COO—, —OCO—, —CONH—, CON(alkyl)-, and —CH=N—; and Cy's each independently represent a phenyl ring, a naphthyl ring, a biphenyl ring, and a cyclohexyl ring which may have at least one substituent selected from F, CN, an alkoxy group, and an alkyl group.

One preferred embodiment of the polyfunctional compound of the present invention is a polyfunctional compound represented by Formula (1a).

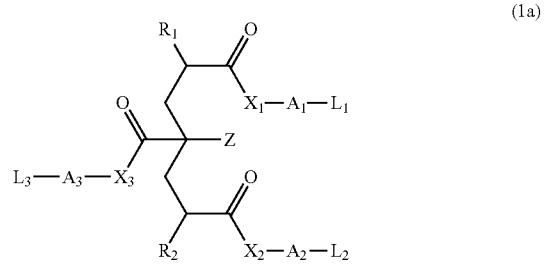

(1a)

In Formula (1a): $R_1$ and $R_2$ each independently represent any of H, $CH_3$, and Cl; Z represents any of H, CN, and $COCH_3$; $X_1$ to each independently represent —O—, —NH—, and —N(alkyl group)-; $A_1$ to $A_3$ each independently represent a divalent connecting group; and $L_1$ to $L_3$ each independently represent a photoisomerization group, a liquid-crystal group, and H, and at least one of $L_1$ to $L_3$ represents a photoisomerization group.

The compound represented by Formula (1a) in which Z represents H can be synthesized, for example, by synthesizing trifunctional acrylic acid in a core portion in accordance with the method described in Macromolecules, 1996, 29, 3511-3514, and thereafter, connecting functional sites. More specifically, methyl cyanoacetate and methyl methacrylate are reacted with sodium ethoxide to synthesize triester, followed by decarboxylation and hydrolysis reactions with an acid catalyst, thereby synthesizing trifunctional acrylic acid in a core portion, and thereafter, subjecting trifunctional acrylic acid in a core portion obtained above and a terminal OH compound having a functional site to an esterification condensation reaction with a condensing agent such as Mitsunobu-type reagent or dicyclohexylcarbodiimide, thereby obtaining an intended polyfunctional compound can be obtained.

As an example of the polyfunctional compound of the present invention in which $R_1$ and $R_2$ each represent H, Z represents CN, $X_1$ to $X_3$ each represent —O—, $A_1$ to $A_3$ each represent an ethylene group in Formula (1a), there is exemplified a polyfunctional compound having the following structure. The compound can be synthesized by subjecting cyanoacetate having an azobenzene structure and acrylate having a cyanobiphenyl structure to ligation with a hydrogen-abstraction catalyst.

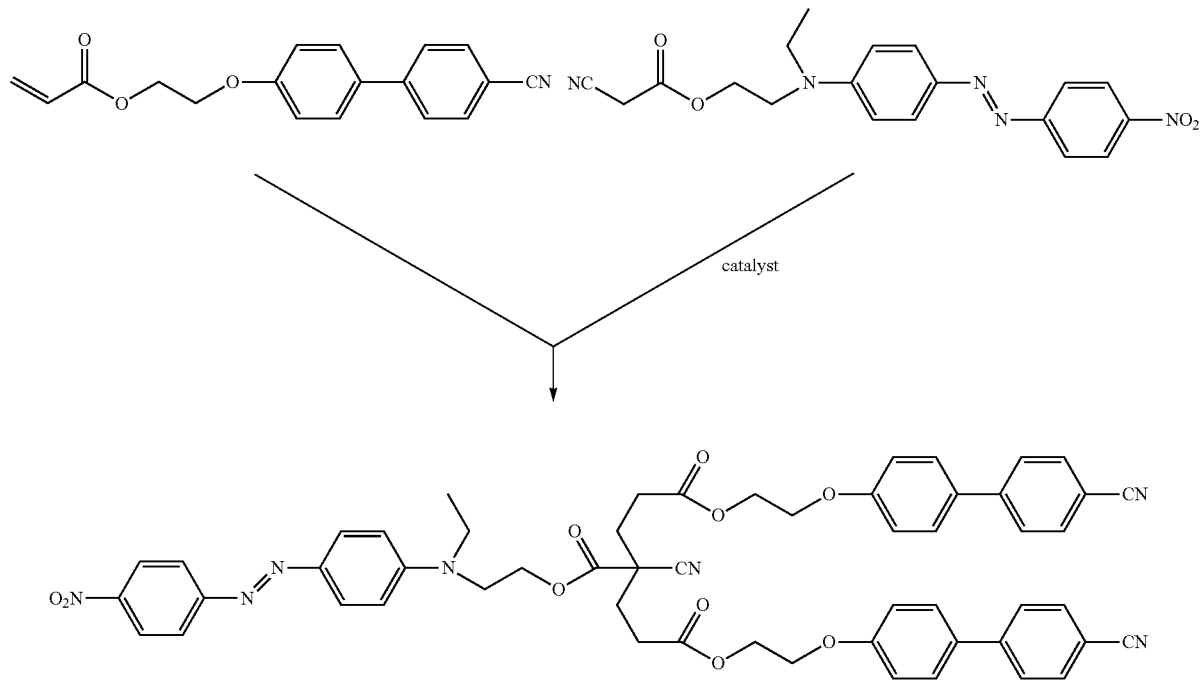

The compound in which Z represents $COCH_3$ instead of CN can be synthesized in the same way by changing cyanoacetate that is used as a material in the above to acetoacetate.

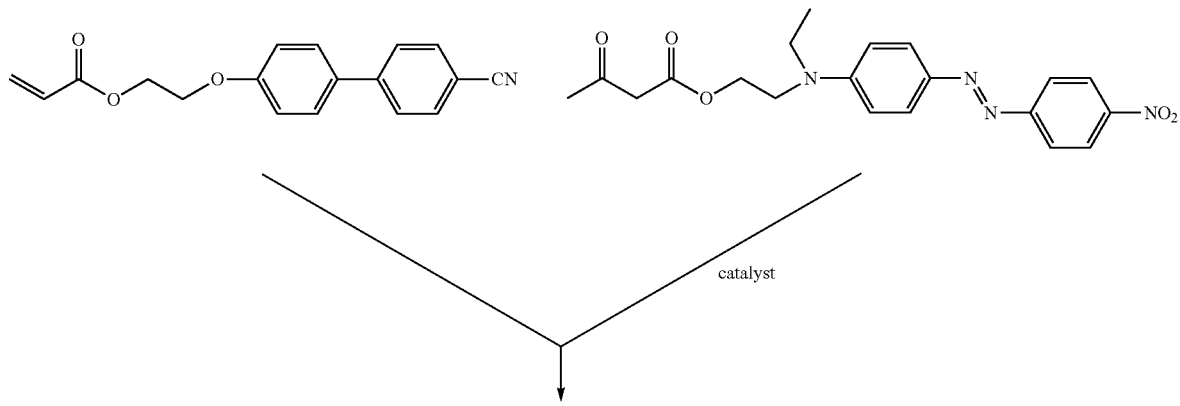

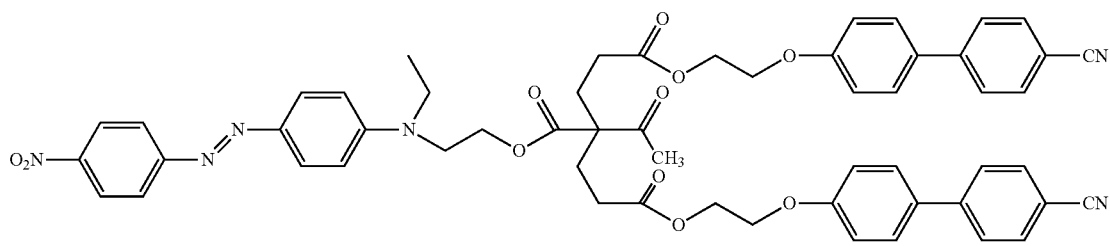

One preferred embodiment of the polyfunctional compound of the present invention is a polyfunctional compound represented by Formula (1b).

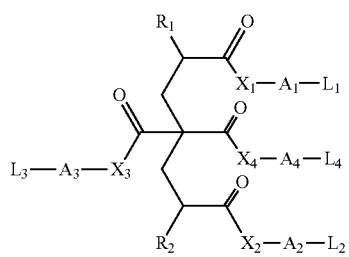

(1b)

In Formula (1b): $R_1$ and $R_2$ each independently represent any of H, $CH_3$, and Cl; $X_1$ to $X_4$ each independently represent any of —O—, —NH—, and —N(alkyl group)-; $A_1$ to $A_4$ each independently represent a divalent connecting group; and $L_1$ to $L_4$ each independently represent any of a photoisomerization group, a liquid-crystal group, and H, and at least one of $L_1$ to $L_4$ represents a photoisomerization group.

As an example of the polyfunctional compound of the present invention in which $R_1$ and $R_2$ each represent $CH_3$, $X_1$ to $X_4$ each represent —O—, and $A_1$ to $A_4$ each represent an ethylene group in Formula (1b), there is exemplified a polyfunctional compound having the following structure. The compound can be synthesized by coupling reaction of methacrylates having an azobenzene structure with malonic diester having a cyanobiphenyl structure using a hydrogen-abstraction catalyst.

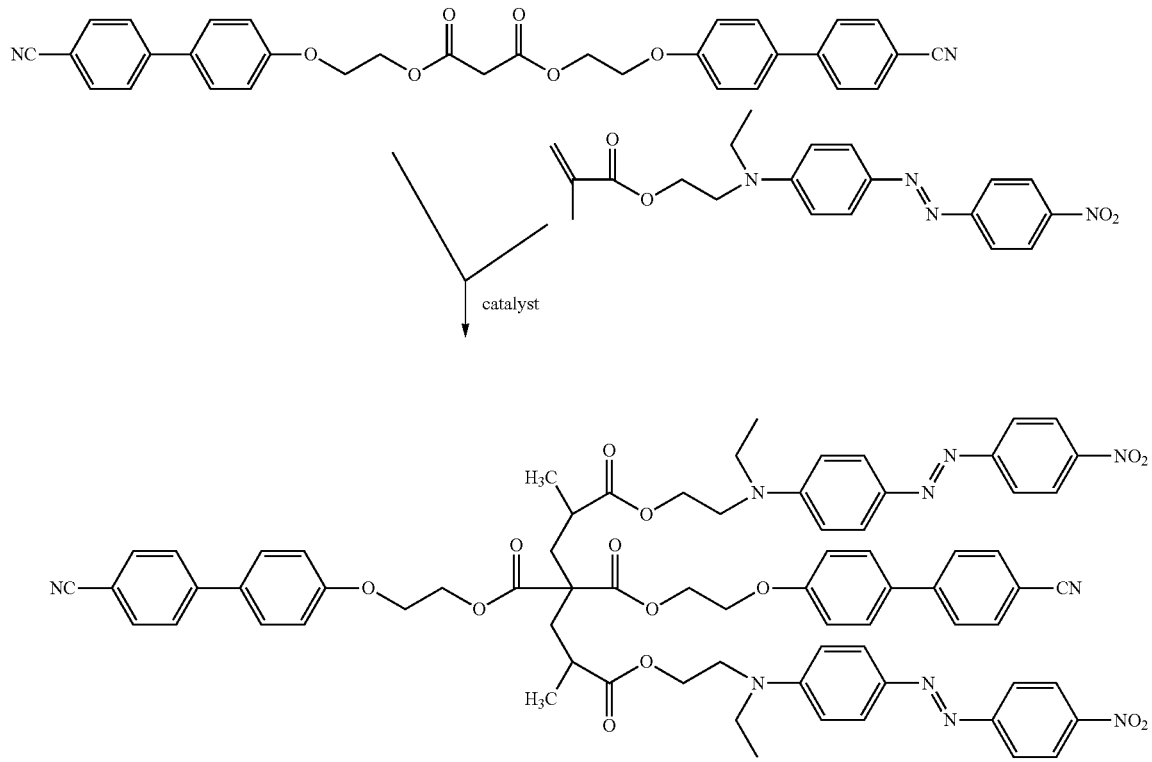

One preferred embodiment of the polyfunctional compound of the present invention is a polyfunctional compound represented by Formula (1c).

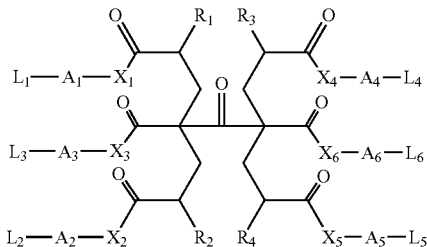

In Formula (1c): $R_1$ to $R_4$ each independently represent any of H, $CH_3$, and Cl; $X_1$ to $X_6$ each independently represent any of —O—, —NH—, and —N(alkyl group)-; $A_1$ to $A_6$ each independently represent a divalent connecting group; and $L_1$ to $L_6$ each independently represent any of a photoisomerization group, a liquid-crystal group, and H, and at least one of $L_1$ to $L_6$ represents a photoisomerization group.

As an example of the polyfunctional compound of the present invention in which $R_1$ to $R_4$ each represent H, $X_1$ to $X_6$ each represent —O—, and $A_1$ to $A_6$ each represent an ethylene group in Formula (1c), there is exemplified a polyfunctional compound having the following structure. The compound can be synthesized by coupling reaction of acrylates having an azobenzene structure with 1,3-diethyl acetonedicarboxylate using a hydrogen-abstraction catalyst.

($n=1$ to 6) represents —O— in the formula can be obtained. Further, if amide is used instead of ester, the compound in which Xn ($n=1$ to 6) represents —NH—, —N(alkyl)- in the formula can be obtained.

As described above, An ($n=1$ to 6) and Ln ($n=1$ to 6) can be introduced by using raw materials having structures thereof.

Cyanoacetates, acetoacetates, malonates, and 1,3-acetonedicarboxylic acid diesters having carbon sandwiched by two electron withdrawing groups are easily deprotonated by the stabilization effect of carbanion generated on carbon to generate anions. For example, the pKa value of hydrogen on carbon at a position adjacent to ketone having only one adjacent carbonyl group is about 20, whereas the pKa value of hydrogen on carbon sandwiched by two ester groups of malonic acid diester is about 10 to 13. Thus, the acidity changes largely. Therefore, malonic diester can easily generate carbanion in the presence of a base having basicity to such a degree as that of amine and alkoxide. The generated carbanion functions as an active nucleophile, and can be subjected to the Michael addition reaction with various electrophiles, for example, (meth)acrylates that are unsaturated carbonyl compounds.

The Michael addition reaction between an active methylene compound and an unsaturated carbonyl compound proceeds efficiently when pKa of active hydrogen of the active methylene compound is 15 or less. Examples thereof include 1,3-cyclohexanedione (pKa=4.8), malonaldehyde (pKa=5.0), meldrum's acid (pKa=5.1), 2,4-pentanedione (pKa=8.9), malononitrile (pKa=11.0), acetoacetate (pKa=11.0), bis(methylsulphonyl)methane (pKa=12.7), cyanoacetate (pKa=13.1), and malonate (pKa=13.5).

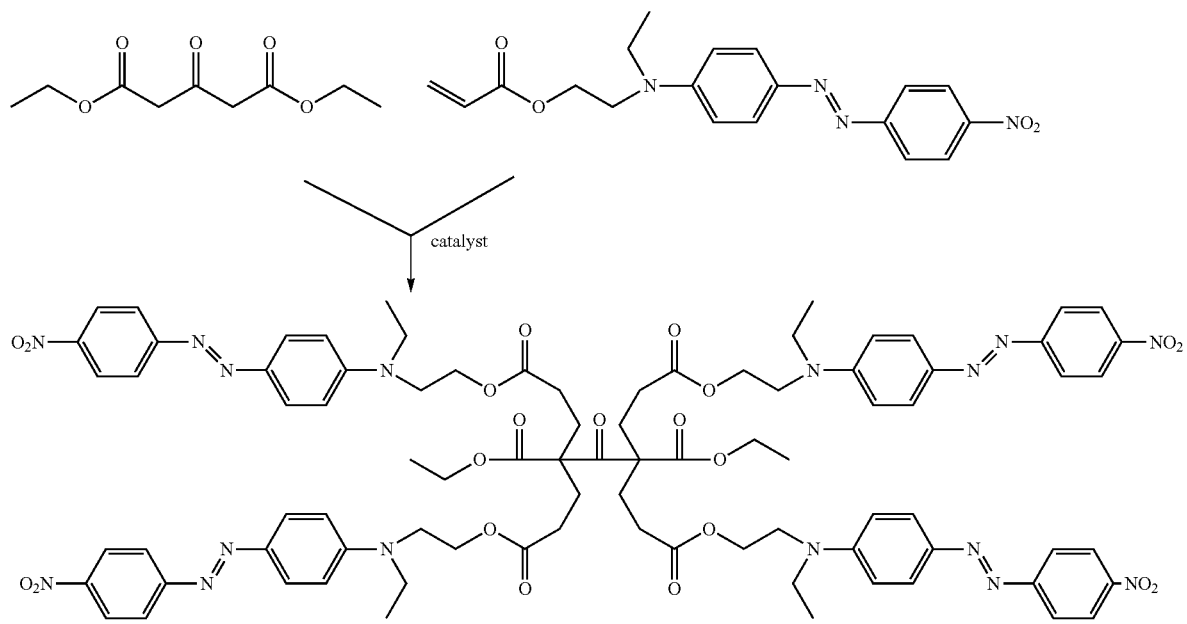

As described above, Rn ($n=1$ to 4) in the formula is derived from (meth)acrylate that can be used as a raw material. Therefore, Rn can be replaced by H if acrylate is used, Rn can be replaced by $CH_3$ if methacrylate is used, and Rn can be replaced by Cl if chloroacrylate is used.

As described above, if cyanoacetates, acetoacetates, malonates, 1,3-acetonedicarboxylic acid diester, or (meth)acrylate are used as a raw material, the compound in which Xn Cyanoacetate, malonate, and acetoacetate are preferred in terms of the general versatility of raw materials. 1,3-acetonedicarboxylic acid diester and complex species thereof can also be used as active methylene compounds.

Catalysts used when abstracting the hydrogen from active methylene compounds (hydrogen-abstraction catalyst) include, as amine-based catalysts, basic ionic liquids such as imidazoline, proline, quinaalkaloid, triazabicyclodecene (TBD), diazabicyclo undecene (DBU), hexahydromethyl pyrimidopyrimidine (MTBD), diazabicyclo nonane (DBN), tetramethyl guanidine (TMG), diazabicyclooctane (DABCO), diisopropyl ethylamine (DIPEA), tetramethyl piperidine (TMP), catalysts in which TBD is carried on a solid-phase such as cross-linked polystyrene or silica gel, and butylmethylimidazolium hydroxide. Further, examples of the base catalyst may include: quaternary ammonium hydroxides such as sodium methoxide, sodium ethoxide, potassium tertiary butoxide, potassium hydroxide, sodium hydroxide, and tetramethyl ammonium hydroxide; sodium metal; lithium diisopropylamide (LDA); and butyl lithium. Further, organic metal catalysts include: ruthenium-based catalysts such as ruthenium cyclooctadiene cyclooctatriene and hydridoruthenium; iron-based catalysts such as trichloride iron and iron acetylacetonate; nickel-based catalysts such as nickel acetyl acetonate, nickel acetate, and nickel salicyl aldehyde; copper-based catalysts; parridium-based catalysts; scandium-based catalysts; lanthanum-based catalysts; and ytterbium-based catalysts. Of those, from the viewpoint of low amounts of side reactions and staining, and versatility of reagent, amine-based catalysts and base catalysts are preferable, and triazabicyclodecene (TBD), diazabicyclo undecene (DBU), and potassium tertiary butoxide are particularly preferably used. Further, in the case of using, although not a general-purpose reagent, a catalyst (product manufactured by Argonaut) in which TBD is carried on a solid phase such as cross-linked polystyrene or silica gel, the catalyst can be removed easily by filtering a reaction solution after the completion of the reaction. Therefore, the purification can be performed easily, and in addition, the solution can be casted as it is without being purified by re-precipitation to form a film. Thus, such a catalyst can be used preferably from an atom economical viewpoint.

The use amount of the hydrogen-abstraction catalyst may be a catalyst amount with respect to raw materials. When the use amount is too large, a side-reaction may be caused, and when the use amount is too small, the reaction may not proceed. The preferable use amount is 0.0001 to 100 mol %, more preferably 0.01 to 10 mol %, and still more preferably 0.1 to 10 mol %.

The reaction temperature of the Michael addition reaction is preferably −78 to 200° C., more preferably 0 to 80° C., and still more preferably around room temperature, i.e., about 25° C.

The reaction time of the Michael addition reaction is preferably 10 seconds to 1 week, more preferably 1 minute to 10 hours, and still more preferably 3 minutes to 5 hours. The reaction may be completed appropriately by checking the reaction progress by analysis means such as thin layer chromatography (TLC), NMR, and infrared spectroscopy.

As the reaction solvent to be used in the Michael addition reaction, any suitable solvent can be adopted as long as it does not react with the hydrogen-abstraction catalyst to be used, does not react with or decompose a base, and preferably dissolves a raw material compound. For example, a solvent that dissolves an intended substance due to the final increase in solubility of a polyfunctional compound may be used although a raw material compound is not completely dissolved therein. The solvent is preferably a dehydrated solvent, but the reaction can also proceed with a solvent that is not dehydrated.

The polyfunctional compound of the present invention may be used alone or in combination.

The polyfunctional compound of the present invention has excellent compatibility. Therefore, it is not necessary to introduce a plurality of functional sites into one polyfunctional compound in order to express a multi-function, and an intended multi-function can be expressed by blending a plurality of polyfunctional compounds, thereby making them soluble. Further, the polyfunctional compound of the present invention has such excellent compatibility, that a film without phase separation can be obtained.

The polyfunctional compound of the present invention can be used for various purposes in combination of other components. Any suitable components in accordance with purposes can be adopted as the other components.

As the other components, any suitable additive can be selected appropriately within a range not impairing the effect of the present invention. Specifically, an antioxidant, a flame retardant, a leveling agent, and a plasticizer can be exemplified, and they may be used alone or in combination. Examples of the antioxidant include a phenol-based compound, an amine-based compound, an organic sulfur-based compound, and a phosphine-based compound.

<<Optical Recording Material>>

The optical recording material of the present invention contains the polyfunctional compound of the present invention. The optical recording material of the present invention can be produced by applying a liquid crystal composition containing the polyfunctional compound of the present invention to a substrate having an alignment regulating force, and subjecting the liquid crystal composition to heating alignment treatment, followed by cooling to room temperature. Further, the optical recording material of the present invention can also be produced by placing the liquid crystal composition containing the polyfunctional compound of the present invention between two substrates at least one of which has an alignment regulating force, and subjecting the liquid crystal composition to heating alignment treatment, followed by cooling to room temperature.

As the substrate (alignment substrate) having an alignment regulating force, there is no particular limit as long as the substrate can align a liquid crystal composition containing the polyfunctional compound of the present invention. For example, a plastic film or sheet whose surface is subjected to rubbing treatment with rayon cloth or the like can be used.

Examples of the plastic are not particularly limited and may include polyolefin of triacetyl cellulose (TAC), polyethylene, polypropylene, and poly(4-methylpentene-1), polyimide, polyimideamide, poyetheramide, polyamide, polyetherether ketone, polyether ketone, polyketone sulfide, polyether sulfone, polysulfone, polyphenylene sulfide, polyphenylene oxide, polyethylene terephthalate, polybutylene terephthalate, polyethylene naphthalate, polyacetal, polycarbonate, acrylic resin, polyvinyl alcohol, polytetrafluoro ethylene, polynorbornene, cellulose-based plastics, an epoxy resin, and a phenol resin. A substrate made of metal such as aluminum, copper, or iron, a ceramic substrate, a glass substrate, or the like, on which the above-mentioned plastic film or sheet is placed, which is subjected to ITO treatment, on which a $SiO_2$ oblique deposition film is formed, or the like, can be used. Further, a laminate in which a stretched film having birefringence subjected to stretching treatment such as uniaxial stretching or the like is laminated as an alignment film on the above-mentioned plastic film or sheet can be used as an alignment substrate. Further, it is preferred that the substrate itself has birefringence, because the rubbing treatment, the lamination of a birefringence film on the surface, and the like are not necessary. As a method of providing a substrate with birefringence, there is a method of performing casting, extrusion molding, or the like, for example, in addition to the stretching treatment in formation of a substrate. In the case where a substrate subjected to alignment treatment is not used, there is also a method of producing an alignment substrate using an electric field or a magnetic field.

In the case where alignment regulation is not required, the liquid crystal composition can be formed on the substrate having no alignment regulating force.

As a method of coating the liquid crystal composition containing the polyfunctional compound of the present invention to a substrate having an alignment regulating force, the liquid crystal composition may be allowed to flow by, for example, roll coating, spin coating, wire bar coating, dip coating, extrusion coating, curtain coating, or spray coating. Of those, spin coating and extrusion coating are preferred in terms of application efficiency.

The temperature conditions of heating alignment treatment after the above application can be appropriately determined in accordance with, for example, the kind of a liquid crystal compound to be used, specifically, a temperature at which the liquid crystal compound exhibits liquid crystallinity. Further, the liquid crystal composition is cooled to room temperature after being subjected to heating alignment treatment, whereby the liquid crystal composition is vitrified and can express an anisotropy function.

<<Optical Recording Medium>>

The optical recording medium of the present invention has an optical recording layer containing the optical recording material of the present invention. It is preferred that the optical recording layer be provided on a substrate (which may be referred to as a base). Further, a reflection layer can also be provided between the optical recording layer and the substrate. Further, a protection layer protecting the optical recording layer can be provided on a surface of the optical recording layer on the opposite side to a surface on which the substrate is provided. Note that the protection layer may be a substrate (i.e., the configuration in which an optical recording layer is sandwiched between a pair of substrates). For the purpose of ensuring the adhesiveness and the like between the substrate and each of the reflection layer and the optical recording layer, or the reflection layer, the optical recording layer, and the protection layer, an intermediate layer can also be provided, if required.

As a shape of the optical recording medium, any suitable shape can be adopted. For example, the optical recording layer is formed two-dimensionally with a constant thickness can be given, and specific examples thereof include a disk shape, a sheet shape, a tape shape, and a drum shape. Further, a disk shape with a hole provided at the center as used in a conventional optical recording medium may be used, because an existing production technology of an optical recording medium and a recording/reproducing system can be used easily.

As the substrate, any suitable material can be adopted as long as the surface thereof is smooth. For example, metal, ceramics, resin, or paper can be used. There is no particular limit to the shape of the substrate. Further, a disk-shaped flat substrate with a hole provided at the center as used in a conventional optical recording medium may be used, because an existing production technology of an optical recording medium and a recording/reproducing system can be used easily.

Specific examples of the materials for the substrate include: glass; acrylic resins such as polycarbonate and polymethyl methacrylate; vinyl chloride-based resins such as polyvinylchloride and vinyl chloride copolymers; epoxy resins; amorphous polyolefin; polyester; and metals such as aluminium. They may be used alone or in combination. Of those materials, from the view point of humidity resistance, dimensional stability, and low-cost, amorphous polyolefin and polycarbonate are preferred, and polycarbonate is particularly preferred.

On the surface of the substrate, guide grooves for tracking and unevenness (pre-grooves) representing information such as an address signal may be formed.

In the case where the optical recording layer is irradiated with light via the substrate during recording or reproduction, it is preferred to use, as a substrate, a material which transmits a wavelength region of light (recording light or reproducing light) to be used. In this case, it is preferred that the transmittance of the wavelength region of light to be used (vicinity of the wavelength region in which the intensity becomes local maximum in the case of laser light) be 90% or more.

Note that, in the case where the reflection layer is provided on the surface of the substrate, it is preferred to form an undercoating layer for the purpose of improving the flatness and enhancing adhesive strength on the surface of the substrate.

Examples of the material for the undercoating layer include: high polymers such as polymethyl methacrylate, an acrylic acid/methacrylic acid copolymer, a styrene/maleic anhydride copolymer, polyvinylalcohols, N-methylol acrylamide, a styrene/vinyltoluene copolymer, chlorosulfonated polyethylene, nitocellulose, polyvinyl chloride, chlorinated polyolefin, polyester, polyimide, a vinyl acetate/vinyl chloride copolymer, an ethylene/vinyl acetate copolymer, polyethylene, polypropylene, and polycarbonate; and surface modifiers such as silane coupling agents.

The undercoating layer can be formed by dissolving or dispersing the material in an appropriate solvent to prepare an application liquid, and thereafter, applying the application liquid to the surface of a substrate by an application method such as spin coating, dip coating, or extrusion coating. The thickness of the undercoating layer is generally preferably in a range of 0.005 µm to 20 µm, and more preferably in a range of 0.01 µm to 10 µm.

It is preferred that the reflection layer be composed of a light reflection substance with a reflectance of laser light of 70% or more. Examples of the light reflection substance include metals and semi-metals such as Mg, Se, Y, Ti, Zr, Hf, V, Nb, Ta, Cr, Mo, W, Mn, Re, Fe, Co, Ni, Ru, Rh, Pd, Ir, Pt, Cu, Ag, Au, Zn, Cd, Al, Ga, In, Si, Ge, Te, Pb, Po, Sn, and Bi, or stainless steel. Those light reflection substances may be used alone, or used as an alloy using two or more kinds thereof. Of those, Cr, Ni, Pt, Cu, Ag, Au, Al, and stainless steel are preferred. Au, Ag, Al, or an alloy thereof is more preferred, and Au, Ag, or an alloy thereof is most preferred.

The reflection layer can be obtained by, for example, forming the light reflection substance on a substrate or a base body by vapor deposition, sputtering, or ion plating. The thickness of the reflection layer is generally preferably in a range of 10 nm to 300 nm, and more preferably in a range of 50 nm to 200 nm.

As the protection layer, any suitable material can be used as long as the material is made of a material having a thickness capable of protecting the optical recording layer mechanically, physically, and chemically under an ordinary use environment. In general, examples of the material include an inorganic material such as a transparent resin and $SiO_2$.

In the case of irradiating the optical recording layer with light via the protection layer during recording and reproduction, it is preferred to use, as the protection layer, a material which transmits a wavelength region of light to be used. In this case, it is preferred that the transmittance of the wavelength region (vicinity of a wavelength region in which the intensity becomes local maximum in the case of laser light) be 90% or more. Note that this also applies to the intermediate layer provided on a surface of the optical recording layer on the side where light is incident, for the purpose of enhancing the adhesiveness and the like.

In the case where the protection layer is made of a resin, a resin film made of polycarbonate, cellulose triacetate, or the like previously formed in a sheet shape can be used, and the resin film is attached to the optical recording layer, whereby a protection layer can be formed. For attachment, it is preferred that the resin film be attached to the optical recording layer via a thermosetting or UV-curable adhesive so as to ensure the adhesive strength, and the adhesive is cured by heat treatment or UV irradiation. As the thickness of the resin film used as the protection layer, any suitable thickness can be adopted as long as the optical recording layer can be protected. The thickness of the resin film used as the protection layer is practically preferably in a range of 30 μm to 200 μm, and more preferably in a range of 50 μm to 150 μm. A protection layer can also be formed by applying a thermoplastic resin, a thermosetting resin, a photocurable resin, or the like instead of such a resin film.

In the case where the protection layer is made of transparent ceramics or a glass material such as $SiO_2$, $MgF_2$, $SnO_2$, or $Si_3N_4$, a protection layer can be formed using sputtering or a sol-gel method. As the thickness of the transparent inorganic material formed as a protection layer, any suitable thickness can be adopted as long as the optical recording layer can be protected. The thickness of the transparent inorganic material used as the protection layer is practically preferably in a range of 0.1 μm to 100 μm, and more preferably in a range of 1 μm to 20 μm.

In the case where the optical recording medium of the present invention is a plane hologram (in the case where a film thickness L of the optical recording layer is smaller than or substantially equal to an interval of interference fringes recorded in the optical recording layer), the film thickness L of the optical recording layer is preferably in a range of 500 nm to 100 μm, and more preferably in a range of 1 μm to 20 μm.

In the case where the optical recording medium of the present invention is a volume hologram (in the case where the film thickness L of the optical recording layer is substantially equal to or several times an interval of the interference fringes recorded in the optical recording layer), the film thickness L of the optical recording layer is preferably in a range of 20 μm to 10 mm, and more preferably in a range of 50 μm to 2 mm.

For forming the optical recording layer, any suitable formation method can be adopted depending upon the material for the optical recording layer. For example, liquid phase film formation such as spraying, spin coating, dipping, roll coating, blade coating, doctor rolling, or screen printing, using an application liquid in which an optical recording material is dissolved, or vapor deposition can be adopted.

The thickness of the optical recording layer to be formed by the above method may not be sufficient for producing a volume hologram type hologram recording medium. In such a case, it is preferred to form a plate-shaped optical recording layer using injection molding or hot pressing. In the case of using those methods, the optical recording layer having a thickness of 0.1 mm or more can be formed easily.

In the case of producing an optical recording medium using such a plate-shaped optical recording layer, the optical recording layer may be sandwiched between a pair of substrates, or in the case where the thickness of the optical recording layer is large and has sufficient rigidity and strength, the optical recording layer can also be used as an optical recording medium.

A method of producing an optical recording medium of the present invention is described. As one preferred embodiment, a method of producing a hologram recording medium is described specifically.

In the case where the optical recording medium of the present invention is a plane hologram, the optical recording medium can be produced by successively laminating an optical recording layer and the like on a substrate depending upon a material used for each layer.

A main flow of a production process of an optical recording medium having a configuration in which an optical recording layer and a protection layer are provided on a substrate is exemplified briefly. First, application liquid in which an optical recording material is dissolved in a solvent is applied to a polycarbonate substrate by spin coating to a desired thickness to form an optical recording layer, followed by drying sufficiently. Next, a UV-curable adhesive is applied uniformly to the optical recording layer by spin coating, and thereafter, the optical recording layer and a cellulose triacetate resin film for forming a protection layer are attached to each other. After that, the resultant laminate is irradiated with UV-light to solidify the adhesive, whereby an optical recording medium having a structure of protection layer/optical recording layer/substrate can be obtained.

In the case where the optical recording medium of the present invention is a volume hologram, it is preferred to form an optical recording layer by injection molding or hot-press sintering, as described above. Therefore, the optical recording medium that is a volume hologram can be produced preferably as follows.

In the case of using injection molding, the optical recording medium can be produced, for example, as follows. First, a disk-shaped molding to be an optical recording layer is produced by injection molding. Next, the disk-shaped molding is sandwiched by a pair of disk-shaped transparent substrates and attached to each other by hot pressing, whereby the molding is allowed to adhere to the transparent substrates by hot-melting. In the step of injection molding, an optical recording material as a raw material is melted by heating and the melted substance is injected to a die to be molded into a disk shape. As an injection molding machine, any of an in-line type injection molding machine in which a plasticizing function and an injection function of a raw material are integrated, and a preplunger type injecting molding machine in which a plasticizing function and an injection function are separated can be used. The conditions and the like for injection molding are preferably an injection pressure of 1,000 to 3,000 kg/cm$^2$ and an injection speed of 5 to 30 mm/sec. Further, in the hot-press step, a plate-shaped molding with a thickness obtained in the step of injection molding is sandwiched between a pair of disk-shaped transparent substrates, and hot pressed under vacuum.

In the optical recording medium thus produced, the optical recording layer is separately formed independently from a substrate by injection molding instead of being formed on the substrate. Therefore, the optical recording layer can be increased in thickness easily and the optical recording medium thus produced is suitable for mass production. Further, the optical recording layer and the transparent substrate are attached to each other by hot pressing, therefore the residual strain of the molding by injection molding is made uniform, and even if the optical recording layer is increased in thickness, the recording characteristics is not impaired by the influence of light absorption and scattering.

In the case of using only hot pressing, an optical recording medium which is a volume hologram can be produced as follows, for example. First, powder resin (resin containing the optical recording material of the present invention) is sandwiched by substrates (pressing members) having a high releasability such as Teflon (Registered Trademark) sheet or the like, and is hot-pressed under vacuum in this state, whereby an optical recording layer is formed directly.

In the case of forming the optical recording layer by vacuum hot pressing, the powder resin is filled as a sample between a pair of pressing members. Next, the pressure is reduced to about 0.1 MPa so as to prevent the generation of air bubbles, and under this condition, the temperature of the resin between the pair of pressing members is raised gradually to a predetermined temperature, and the sample is pressed via the pressing members. It is preferred that the heating temperature be set to be a glass transition temperature (Tg) or higher of the optical recording material, and the pressing pressure is set to be 0.01 to 0.1 t/cm$^2$. The hot pressing is performed for a predetermined period of time, and thereafter, the heating and pressing are stopped, and the sample is taken out after being cooled to room temperature.

The optical recording material sandwiched between a pair of pressing members is melted by heating by performing hot pressing, and the optical recording material is cooled, whereby a plate-shaped optical recording layer is obtained. Finally, the pressing members are removed to obtain an optical recording medium. For example, in the case of using a polymer compound having Tg of about 50° C. as an optical recording material, the polymer compound is hot-pressed by heating to about 70° C., whereby the optical recording layer can be formed to a desired thickness easily. Further, the residual strain does not occur by hot pressing. If required, for the purpose of enhancing damage resistance and moisture resistance of the optical recording medium formed of the optical recording layer, a protection layer and the like may be provided.

In the optical recording medium thus produced, the optical recording layer can be increased in thickness easily. Further, the optical recording layer is formed by hot pressing, therefore the residual strain and the like of the molding do not occur, and even when the recording layer is increased in thickness, the recording characteristics are not impaired by the influence of light absorption and scattering.

The optical recording medium of the present invention has an optical recording layer containing the optical recording material of the present invention, and records information on the optical recording layer using at least one of an absorption change, a refractive index change, and a shape change by light irradiation. Examples of the optical recording method include hologram recording, light absorptivity modulation recording, light reflectance modulation recording, and photoinduced relief formation. Of those, an optical recording method preferable for an optical recording medium of the present invention is hologram recording.

A hologram can be recorded on the optical recording medium of the present invention due to the modulation of an amplitude, a phase, or a polarization direction of light of an object, and the optical recording medium of the present invention can be used as an excellent optical recording medium even in high-speed transfer using a large capacity based on volume type recording and parallelism of digital data to be recorded.

<<Optical Recording/Reproducing Apparatus>>

An optical recording/reproducing apparatus of the present invention includes an optical recording medium of the present invention.

The optical recording/reproducing apparatus of the present invention is capable of recording/reproducing information using an optical recording medium of the present invention.

The optical recording/reproducing apparatus of the present invention preferably records information in the optical recording medium of the present invention as a hologram. In the optical recording/reproducing apparatus of the present invention, preferably, the polarization state of light of an object and the polarization state of reference light during recording are different.

<<Other Uses of Polyfunctional Compound of the Present Invention>>

The polyfunctional compound of the present invention can be applied to any suitable use, in addition to the optical recording material. For example, when the polyfunctional compound of the present invention is irradiated with light, the photoisomerization of a photoisomerization site can cause the modulation of a refractive index, which causes a refractive index difference between a light-irradiated part and a part not irradiated with light, and because capable of being applied to an optical waveguide. Therefore, the polyfunctional compound of the present invention can be applied to an optical waveguide material. More specifically, the optical waveguide material of the present invention contains the polyfunctional compound of the present invention. Further, the polyfunctional compound of the present invention can form a film, and can be used by being changed to any shape by spin coating and thermal melting. Therefore, the polyfunctional compound of the present invention can form a film and is excellent in photosensitivity. Thus, the polyfunctional compound of the present invention can be applied to a photo-alignment film material. That is, the photo-alignment film material of the present invention contains the polyfunctional compound of the present invention.

EXAMPLE

Hereinafter, the present invention is described specifically by way of examples, but the present invention is not limited thereto. Unless otherwise specified, parts and percent in examples are expressed in terms of weight.

Example 1

Acrylate (2.62 g, 5.24 mmol) having a liquid-crystal group and cyanoacetate (1.00 g, 2.62 mmol) having a Disperse Red 1 structure which was an azobenzene-based photoisomerization group were dissolved in tetrahydrofuran (30 mL) under a nitrogen atmosphere, and one drop of diazabicycloundecene (DBU) was added to the mixture, followed by stirring at room temperature for 10 minutes. 10 drops of a hydrochloric acid aqueous solution were added thereto to neutralize the reaction solution. Then, a precipitate generated when the solution was dropped to methanol was filtered. The precipitate was dissolved in tetrahydrofuran again and reprecipitated into methanol, and the precipitate was filtered and dried by heating in vacuum, whereby a polyfunctional compound (1) having one azobenzene site and two liquid crystal sites was obtained (3.00 g, 2.17 mmol, 83%).

The obtained polyfunctional compound (1) (molecular weight: 1380.4) was measured for a molecular weight by MALDI-TOFMS measurement, and as a result, only ions having m/z of 1383.5 and 1405.6 were detected. Those ions corresponded to ions in which protons were added to the polyfunctional compound (1) and ions in which sodium was added to the polyfuncitonal compound (1), whereby it was found that the polyfunctional compound (1) was obtained.

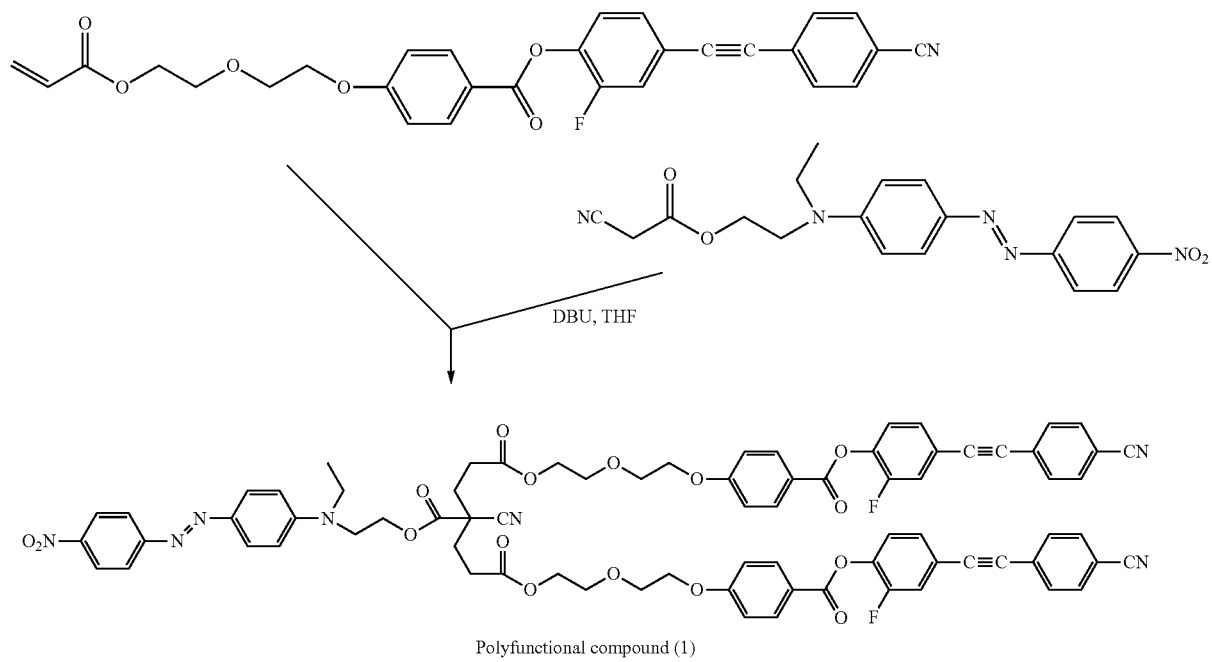

Polyfunctional compound (1)

Example 2

Acrylate (1.64 g, 3.28 mmol) having a liquid-crystal group and cyanoacetate (0.70 g, 1.64 mmol) having another liquid-crystal group were dissolved in dimethylformamide (10 mL) under a nitrogen atmosphere, and one drop of diazabicycloundecene (DBU) was added to the mixture, followed by stirring at room temperature for 30 minutes. 10 drops of a hydrochloric acid aqueous solution were added thereto to neutralize the reaction solution. Then, a precipitate generated when the solution was dropped to methanol was filtered. The precipitate was dissolved in tetrahydrofuran again and reprecipitated into methanol, and the precipitate was filtered and dried by heating in vacuum, whereby a polyfunctional compound (2) having one azobenzene site and two liquid crystal sites was obtained (201 g, 1.41 mmol, 83%).

The obtained polyfunctional compound (2) (molecular weight: 1425.4) was measured for a molecular weight by MALDI-TOFMS measurement, and as a result, only ions having m/z of 1450.4 were detected. Those ions corresponded to ions in which sodium was added to the polyfuncitonal compound (2), whereby it was found that the polyfunctional compound (2) was obtained.

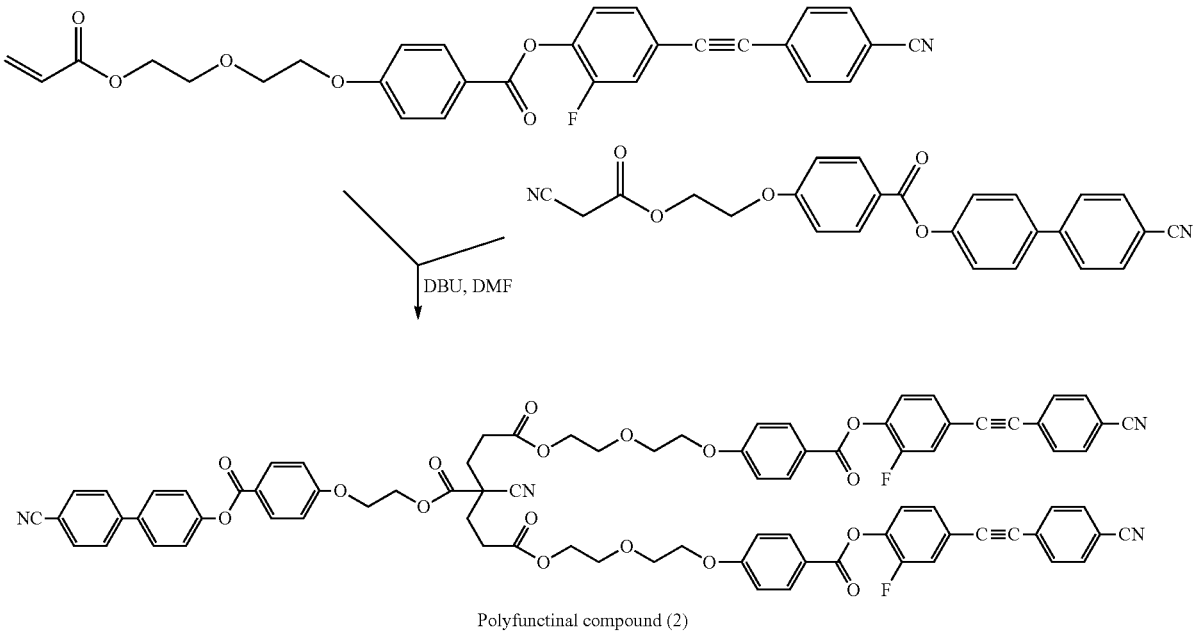

Polyfunctinal compound (2)

Example 3

Cyanobiphenyl acrylate (1.38 g, 5.53 mmol) and cyanoacetate(1.00 g, 2.77 mmol) having a Disperse Red 1 structure which was an azobenzene-based photoisomerization group were dissolved in tetrahydrofuran (25 mL) under a nitrogen atmosphere, and one drop of diazabicycloundecene (DBU) was added to the mixture, followed by stirring at room temperature for 15 minutes. 10 drops of a hydrochloric acid aqueous solution were added to neutralize the reaction solution. Then, a precipitate generated when the solution was dropped to methanol was filtered. The precipitate was dissolved in tetrahydrofuran and reprecipitated into methanol, and the precipitate was filtered and dried by heating in vacuum, whereby a polyfunctional compound (3) having one azobenzene site and two liquid crystal sites was obtained (1.88 g, 2.19 mmol, 79%).

The obtained polyfunctional compound (3) (molecular weight: 879.9) was measured for a molecular weight by MALDI-TOFMS measurement, and as a result, only ions having m/z of 882.1 and 904.3 were detected. Those ions corresponded to ions in which protons were added to the polyfunctional compound (3) and ions in which sodium was added to the polyfuncitonal compound (3), whereby it was found that the polyfunctional compound (3) was obtained.

Example 4

Acrylate (3.51 g, 14.07 mmol) having a liquid-crystal group and cyanoacetate (3.00 g, 7.04 mmol) having another liquid-crystal group were dissolved in dimethyl formamide (50 mL) under a nitrogen atmosphere, and two drops of diazabicycloundecene (DBU) were added to the mixture, followed by stirring at room temperature for 15 minutes. 15 drops of a hydrochloric acid aqueous solution were added to neutralize the reaction solution. Then, a precipitate generated when the solution was dropped to methanol was filtered. The precipitate was dissolved in tetrahydrofuran again and reprecipitated into methanol, and the precipitate was filtered and dried by heating in vacuum, whereby a polyfunctional compound (4) having one azobenzene site and two liquid crystal sites was obtained (6.18 g, 6.69 mmol, 95%).

The obtained polyfunctional compound (4) (molecular weight: 924.9) was measured for a molecular weight by MALDI-TOFMS measurement, and as a result, only ions having m/z of 949.9 were detected. Those ions corresponded to ions in which sodium was added to the polyfuncitonal compound (4), whereby it was found that the polyfunctional compound (4) was obtained.

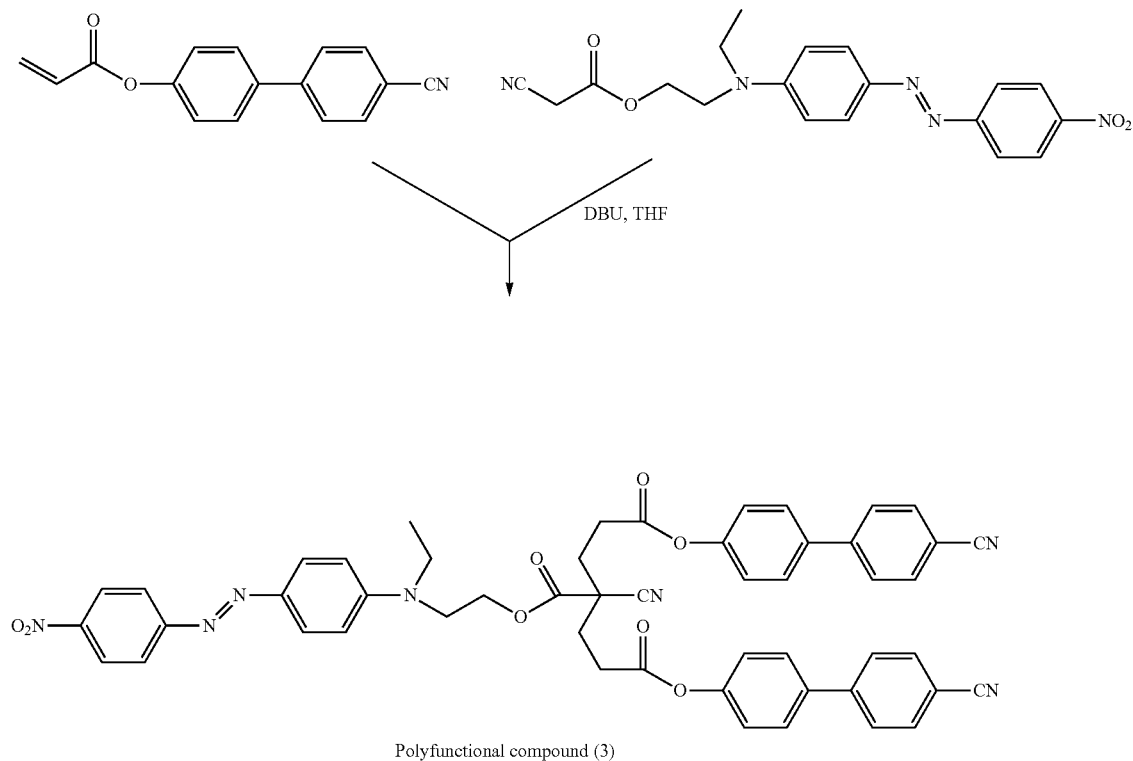

Polyfunctional compound (3)

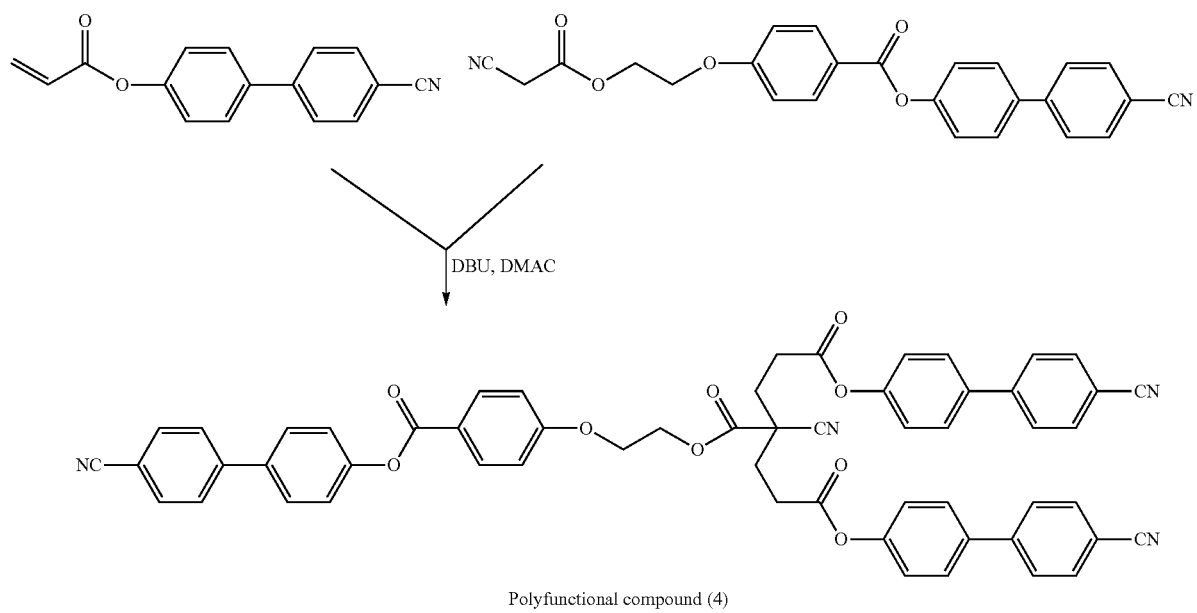

Polyfunctional compound (4)

Production Example 1

Sample Production (A)

30 wt % cyclohexanone solutions containing the polyfunctional compound (1) obtained in Example 1 and the polyfunctional compound (2) obtained in Example 2 in weight ratios of (2)/(1)=1/3, 2/2, and 3/1, respectively, were prepared. Those solutions were spin-coated onto a glass substrate subjected to polyvinyl alcohol thin film treatment and rubbing treatment, followed by drying a solvent and liquid crystal alignment treatment at 130° C. for 2 minutes on a hot plate, whereby thin film samples having a thickness of 3 μm in which liquid crystal molecules and azobenzene molecules were uniaxially aligned were obtained.

Production Example 2

Sample Production (B)

30 wt % cyclohexanone solutions containing the polyfunctional compound (3) obtained in Example 3 and the polyfunctional compound (4) obtained in Example 4 in weight ratios of (4)/(3)=1/6, 1/3, 2/2, and 3/1, respectively, were prepared. Those solutions were spin-coated onto a glass substrate subjected to polyvinyl alcohol thin film treatment and rubbing treatment, followed by drying a solvent and liquid crystal alignment treatment at 130° C. for 2 minutes on a hot plate, whereby thin film samples having a thickness of 3 μm in which liquid crystal molecules and azobenzene molecules were uniaxially aligned were obtained.

[Evaluation Regarding Induction of Birefringence by Single Flux Exposure]

FIG. 1 is a schematic diagram of an optical experiment for confirming that birefringence is induced into a material by light irradiation.

As a sample for evaluating characteristics, an alignment film (thickness: 3 μm) of (2)/(1)=1/3 obtained in Sample Production (A) was used.

As a light source for inducing birefringence, a diode excited solid laser of 532 nm (S polarized light, 28 mW/cm$^2$) was used. The surface of the sample was irradiated with light from the light source in a normal direction. The surface of the sample was also irradiated with a He—Ne laser of 633 nm (S polarized light, 290 mW/m$^2$) tilted by 49.5° with respect to a normal line of a back surface of the sample. The transmitted He—Ne laser light was measured for a change in intensity through a polarizing plate (an optical axis was immobilized at 0°).

As a result of the measurements, the amount of transmitted light was reduced by 20% by irradiation for 5 to 6 minutes. Even when this sample was observed under natural light, there was no difference between a light-irradiated surface and a surface not irradiated with light. However, when the sample was observed under Cross-Nicols, there was a difference in the amount of transmitted light between the light-irradiated area and the area not irradiated with light. Thus, it was found that the decrease in the amount of transmitted light was caused by birefringence. Further, there was no change in the amount of transmitted light even by irradiation of only a He—Ne laser for 15 minutes, and hence it was found that the birefringence by the Weigert effect was caused by a 532 nm laser.

When the sample was heated to 130° C. for several minutes on a hot plate and gradually cooled, it was found by the observation under Cross-Nicols that the birefringence was lost. When the sample was placed on an optical experiment platform again and measured for intensity of transmitted light of a He—Ne laser, it was found that the decreased amount of transmitted light was recovered to an original value.

When the sample was irradiated with the 532 nm laser again, a similar decrease in intensity of transmitted light was observed. Even when the operation was repeated 5 times, the property thereof was not changed. Thus, it was found that it is possible to repeat the induction of birefringence by the 532 nm laser.

[Method of Evaluating Hologram Recording Characteristics]

Figure 2:
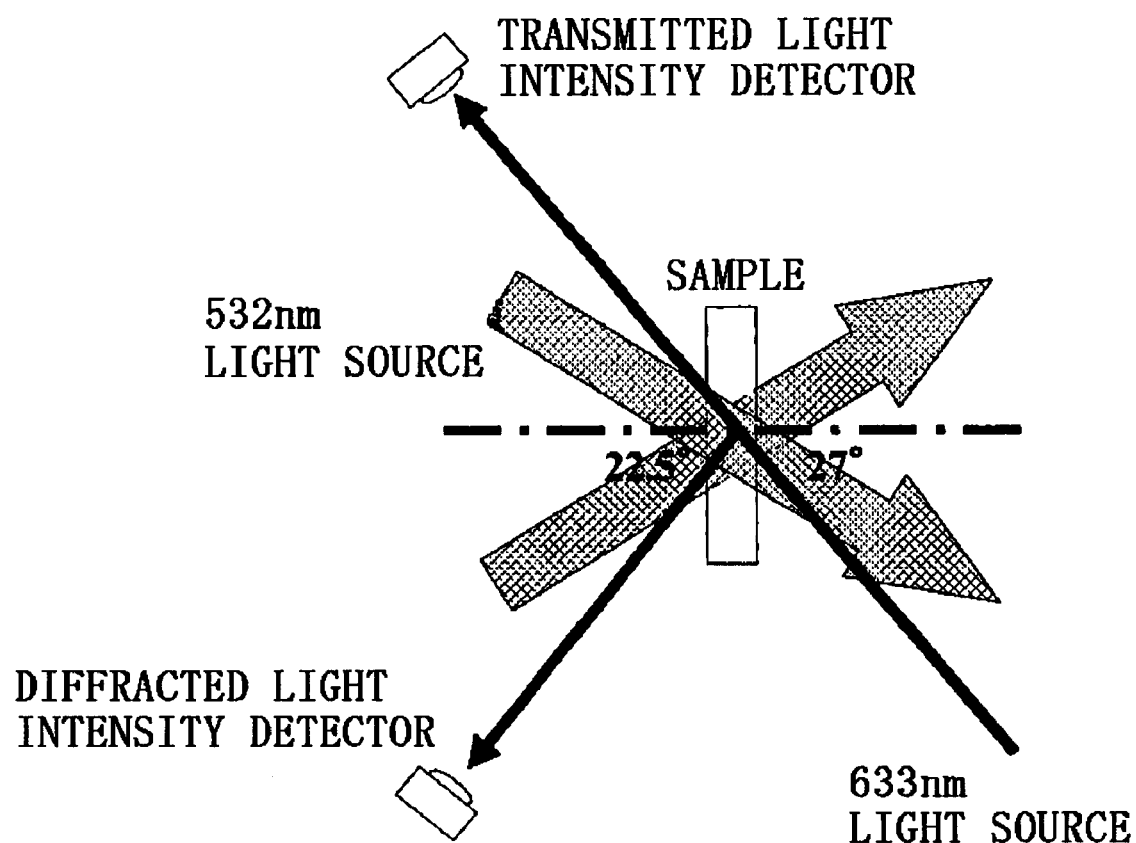
FIG. 2 is a schematic diagram of an optical experiment used for evaluating hologram recording characteristics.

FIG. 2 is a schematic diagram of an optical experiment used for the evaluation of hologram recording characteristics. As writing light, a diode excited solid laser of 532 nm (S polarized light, 100 mW/cm$^2$) was used as a light source. A beam output from the light source was divided into two with a beam splitter to obtain two fluxes, and the respective beams were reflected from a mirror so as to each form an angle of 22.5° (nip angle of two beams of 45°) with respect to a normal line of the surface of the sample to irradiate the sample for evaluation of characteristics. At this time, the back surface of the sample was irradiated with a 633 nm He—Ne laser (S polarized light, 290 mW/cm$^2$) tilted by 27° with respect to the normal line of the surface of the sample from the back surface of the sample.

The intensity of the transmitted light and the intensity of diffracted light of the He—Ne laser of a diffraction grating were substituted into Calculation Equation 1, whereby a diffraction efficiency (%) was obtained.

Diffraction efficiency (%)=Intensity of diffracted light/(Intensity of diffracted light+Intensity of transmitted light)×100  (Calculation Equation 1)

Further, sensitivity (cm$^2$/J) was obtained by Calculation Equation 2, from the time during which the diffraction efficiency reached maximum set to be a response time, together with the exposure intensity (0.1 W/cm$^2$) of the 532 nm laser.

Sensitivity (cm$^2$/J)=(Maximum diffraction efficiency)$^{1/2}$/(0.1× Response time (sec))  (Calculation Equation 2)

[Evaluation of Hologram Recording Characteristics (A1)]

Figure 3:
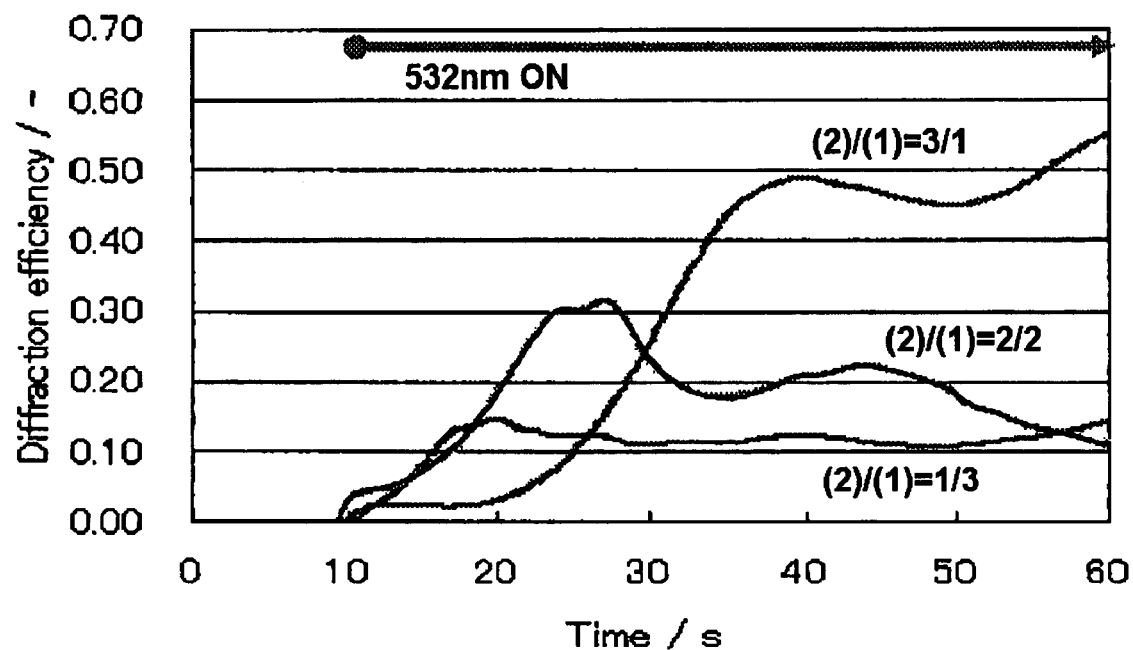
FIG. 3 is a graph diagram showing a relationship between a diffraction efficiency and a time regarding thin film samples each containing a polyfunctional compound (2) and a polyfunctional compound (1) at a ratio of polyfunctional compound (2)/polyfunctional compound (1)=1/3, 2/2, 3/1.

FIG. 3 is a graph showing a relationship between a diffraction efficiency and a time regarding thin film samples containing the polyfunctional compound (1) and the polyfunctional compound (2) produced in Production Example 1 in weight ratios of (2)/(1)=1/3, 2/2, and 3/1, respectively.

All thin film samples exhibited a maximum diffraction efficiency (10 to 50%) during 10 to 30 seconds from the commencement of 532 nm laser exposure. It was found from those values that all thin film samples had a sensitivity of 0.029 to 0.05 cm$^2$/J and satisfactory hologram recording characteristics.

[Evaluation of Hologram Recording Characteristics (A2)]

Figure 4:
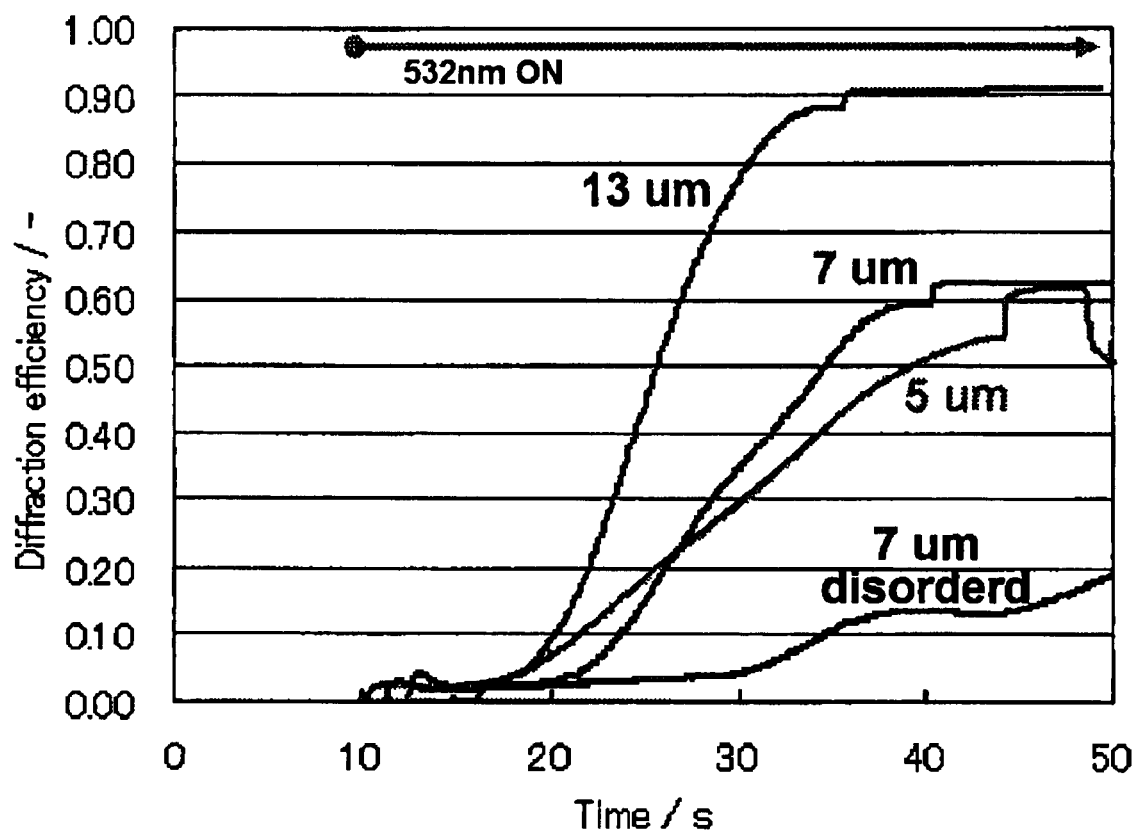
FIG. 4 is a graph diagram showing a relationship between a diffraction efficiency and a time regarding thin film samples each having a thickness of 5 μm, 7 μm, and 13 μm and each containing the polyfunctional compound (2) and the polyfunctional compound (1) at a ratio of polyfunctional compound (2)/polyfunctional compound (1)=3/1.

Thin film samples were produced by increasing the thickness of a thin film sample containing the polyfunctional compound (1) and the polyfunctional compound (2) produced in Production Example 1 in a weight ratio of (2)/(1)=3/1 to 5 μm, 7 μm, and 13 μm, and hologram recording characteristics thereof were evaluated. FIG. 4 shows the results.

As is understood from FIG. 4, the diffraction efficiency was increased to about 90% at maximum by increasing the thickness of an alignment film. In a conventional liquid crystal-azobenzene complex polymer, such an aligned thick film was not able to be obtained. However, a thick film was able to be produced using the polyfunctional compound of the present invention. Thus, an optical recording element with a high diffraction efficiency value has become able to be produced.

In FIG. 4, a curve of a diffraction efficiency value indicated as "7 um disordered" represents the results obtained by performing laser exposure evaluation with respect to an incompletely aligned sample having a thickness of 7 μm and aligned insufficiently, and thus, a diffraction efficiency is not increased sufficiently. It was found that the evaluation of optical recording should have been performed after the alignment was conducted securely.

[Evaluation of Hologram Recording Characteristics (B)]

Figure 5:
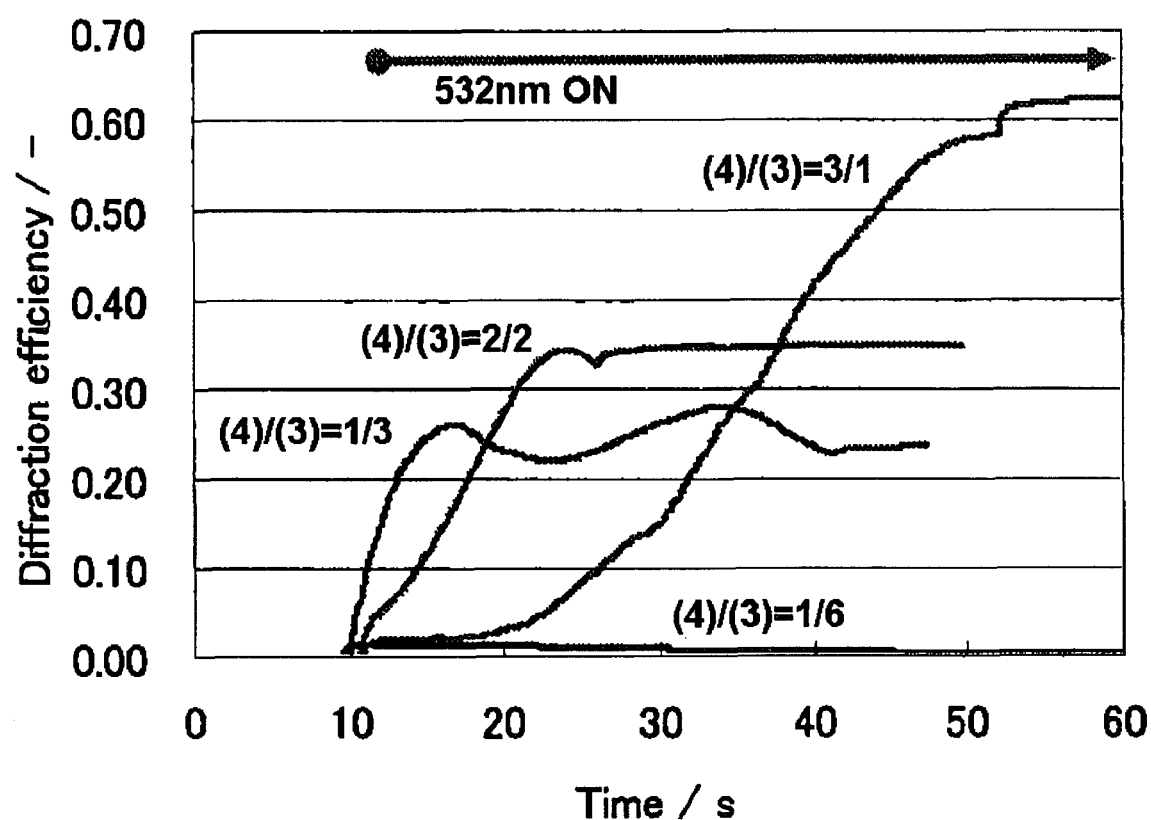
FIG. 5 is a graph diagram showing a relationship between a diffraction efficiency and a time regarding thin film samples each containing a polyfunctional compound (4) and a polyfunctional compound (3) at a ratio of polyfunctional compound (4)/polyfunctional compound (3)=1/6, 1/3, 2/2, and 3/1.

FIG. 5 is a graph showing a relationship between a diffraction efficiency and a time regarding thin film samples containing the polyfunctional compound (3) and the polyfunctional compound (4) produced in Production Example 2 in weight ratios of (4)/(3)=1/6, 1/3, 2/2, and 3/1, respectively.

All thin film samples exhibited a maximum diffraction efficiency (20 to 60%) during 5 to 40 seconds from the commencement of 532 nm laser exposure. It was found from those values that all thin film samples had a sensitivity of 0.02 to 0.12 cm$^2$/J and satisfactory hologram recording characteristics. In particular, it was found that the thin film sample containing the polyfunctional compound (3) and the polyfunctional compound (4) in a weight ratio of (4)/(3)=3/1 had an extremely high sensitivity.

INDUSTRIAL APPLICABILITY

The polyfunctional compound of the present invention enables a material to be obtained, which controls birefringence by light irradiation to modulate a refractive index, and can be applied to optical data recording by being formed appropriately or optical elements such as a photo-alignment film and an optical waveguide material. The element thus obtained is more excellent for producing a thick film sample without any alignment defects such as phase separation, than that obtained by using a conventional polymer material, and is further excellent in optical recording characteristics (diffraction efficiency value and sensitivity in writing thereof).

The invention claimed is:

1. A polyfunctional compound which is represented by Formula (1a):

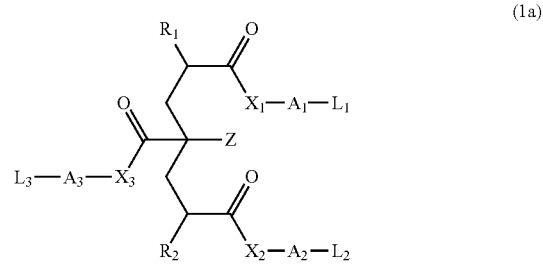

(1a)

where: $R_1$ and $R_2$ each independently represent any of H, $CH_3$, and Cl; Z represents any of H, CN, and $COCH_3$; $X_1$ to $X_3$ each independently represent any of —O—, —NH—, and —N(alkyl group)-; $A_1$ to $A_3$ each independently represent a divalent connecting group; and $L_1$ to $L_3$ each independently represent any of a photoisomerization group, a liquid-crystal group, and H, and at least one of $L_1$ to $L_3$ represents a photoisomerization group.

2. A polyfunctional compound which is represented by Formula (1b):

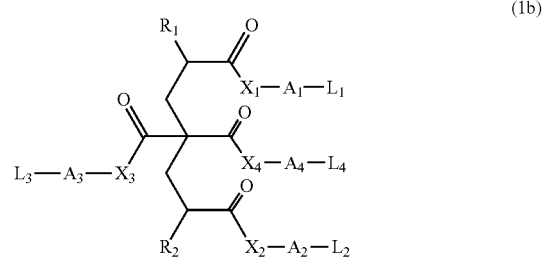

(1b)

where: $R_1$ and $R_2$ each independently represent any of H, $CH_3$, and Cl; $X_1$ to $X_4$ each independently represent any of —O—, —NH—, and —N(alkyl group)-; $A_1$ to $A_4$ each independently represent a divalent connecting group; and $L_1$ to $L_4$ each independently represent any of a photoisomerization group, a liquid-crystal group, and H, and at least one of $L_1$ to $L_4$ represents a photoisomerization group.

3. A polyfunctional compound which is represented by Formula (1c):

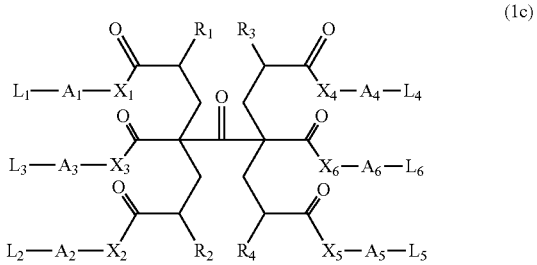

where: $R_1$ to $R_4$ each independently represent any of H, $CH_3$, and Cl; $X_1$ to $X_6$ each independently represent any of —O—, —NH—, and —N(alkyl group)-; $A_1$ to $A_6$ each independently represent a divalent connecting group; and $L_1$ to $L_6$ each independently represent any of a photoisomerization group, a liquid-crystal group, and H, and at least one of $L_1$ to $L_6$ represents a photoisomerization group.

4. A polyfunctional compound according to claim 1, wherein the photoisomerization group has a structure represented by Formula (2):

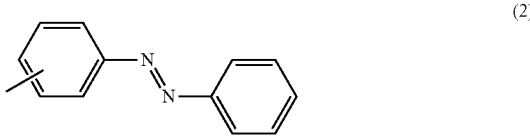

where each aromatic ring may have one or more substituents.

5. A polyfunctional compound according to claim 1, wherein the liquid-crystal group has a structure represented by any of Formulae (3a) to (3g):

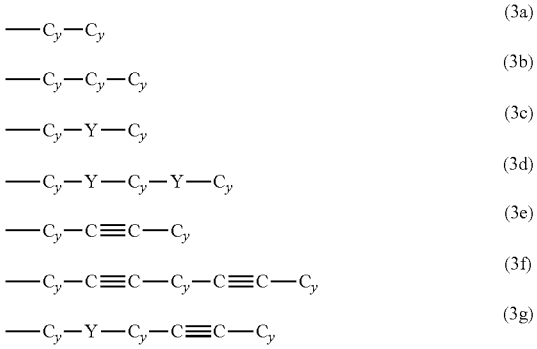

where: Y's represent any of —COO—, —OCO—, —CONH—, CON(alkyl)-, and —CH=N—; and Cy's each independently represent a phenyl ring, a naphthyl ring, a biphenyl ring, or a cyclohexyl ring which may have at least one substituent selected from F, CN, an alkoxy group, and an alkyl group.

6. An optical recording material comprising the polyfunctional compound according to claim 1.

7. An optical recording medium comprising an optical recording layer containing the optical recording material according to claim 6.

8. An optical recording/reproducing apparatus comprising the optical recording medium according to claim 7.

9. An optical waveguide material comprising the polyfunctional compound according to claim 1.

10. A photo-alignment film material comprising the polyfunctional compound according to claim 1.

11. A polyfunctional compound according to claim 2, wherein the photoisomerization group has a structure represented by Formula (2):

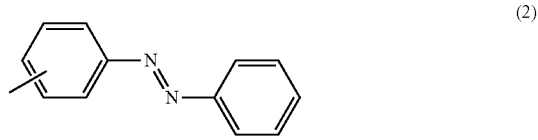

where each aromatic ring may have one or more substituents.

12. A polyfunctional compound according to claim 2, wherein the liquid-crystal group has a structure represented by any of Formulae (3a) to (3g):

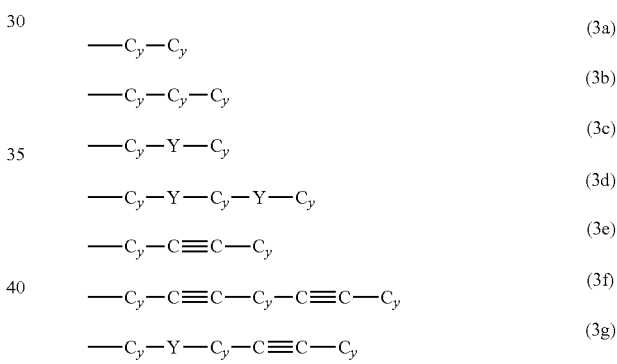

where: Y's represent any of —COO—, —OCO—, —CONH—, CON(alkyl)-, and —CH=N—; and Cy's each independently represent a phenyl ring, a naphthyl ring, a biphenyl ring, and a cyclohexyl ring which may have at least one substituent selected from F, CN, an alkoxy group, and an alkyl group.

13. An optical recording material comprising the polyfunctional compound according to claim 2.

14. An optical recording medium comprising an optical recording layer containing the optical recording material according to claim 13.

15. An optical recording/reproducing apparatus comprising the optical recording medium according to claim 14.

16. An optical waveguide material comprising the polyfunctional compound according to claim 2.

17. A photo-alignment film material comprising the polyfunctional compound according to claim 2.

18. A polyfunctional compound according to claim 3, wherein the photoisomerization group has a structure represented by Formula (2):

(2)

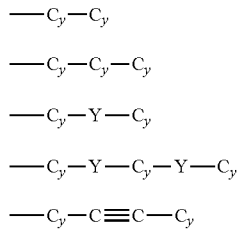

where each aromatic ring may have one or more substituents.

19. A polyfunctional compound according to claim 3, wherein the liquid-crystal group has a structure represented by any of Formulae (3a) to (3g):

—$C_y$—$C_y$ (3a)

—$C_y$—$C_y$—$C_y$ (3b)

—$C_y$—Y—$C_y$ (3c)

—$C_y$—Y—$C_y$—Y—$C_y$ (3d)

—$C_y$—C≡C—$C_y$ (3e)

—$C_y$—C≡C—$C_y$—C≡C—$C_y$ (3f)

—$C_y$—Y—$C_y$—C≡C—$C_y$ (3g)

where: Y's represent any of —COO—, —OCO—, —CONH—, CON(alkyl)-, and —CH=N—; and Cy's each independently represent a phenyl ring, a naphthyl ring, a biphenyl ring, or a cyclohexyl ring which may have at least one substituent selected from F, CN, an alkoxy group, and an alkyl group.

20. An optical recording material comprising the polyfunctional compound according to claim 3.

21. An optical recording medium comprising an optical recording layer containing the optical recording material according to claim 20.

22. An optical recording/reproducing apparatus comprising the optical recording medium according to claim 21.

23. An optical waveguide material comprising the polyfunctional compound according to claim 3.

24. A photo-alignment film material comprising the polyfunctional compound according to claim 3.

* * * * *